(12) United States Patent
Wang et al.

(10) Patent No.: US 11,279,742 B2
(45) Date of Patent: *Mar. 22, 2022

(54) RECOMBINANT HUMAN EPO-FC FUSION PROTEINS WITH PROLONGED HALF-LIFE AND ENHANCED ERYTHROPOIETIC ACTIVITY IN VIVO

(71) Applicant: Novagen Holding Corporation, Grand Cayman (KY)

(72) Inventors: Haitao Wang, Vancouver (CA); Yong Du, Vancouver (CA); Rui Zhang, Vancouver (CA); Jing Xu, Vancouver (CA); Longbin Liu, West Vancouver (CA)

(73) Assignee: NOVAGEN HOLDING CORPORATION, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 15/992,068

(22) Filed: May 29, 2018

(65) Prior Publication Data

US 2019/0070307 A1  Mar. 7, 2019

Related U.S. Application Data

(63) Continuation of application No. 12/162,320, filed as application No. PCT/CA2007/000107 on Jan. 25, 2007, now Pat. No. 10,117,949, which is a continuation-in-part of application No. 11/340,661, filed on Jan. 27, 2006, now Pat. No. 7,625,564.

(51) Int. Cl.
| | |
|---|---|
| *A61K 38/18* | (2006.01) |
| *C07K 14/505* | (2006.01) |
| *C07K 16/00* | (2006.01) |
| *A61K 9/00* | (2006.01) |
| *A61K 47/68* | (2017.01) |
| *A61K 38/00* | (2006.01) |

(52) U.S. Cl.
CPC .......... *C07K 14/505* (2013.01); *A61K 9/0019* (2013.01); *A61K 47/6811* (2017.08); *A61K 38/00* (2013.01); *C07K 2317/53* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,116,964 A | 5/1992 | Capon et al. |
| 5,618,698 A | 4/1997 | Lin |
| 5,908,626 A | 6/1999 | Chang et al. |
| 5,916,773 A | 6/1999 | Mele et al. |
| 6,096,871 A | 8/2000 | Presta et al. |
| 6,165,476 A | 12/2000 | Strom et al. |
| 6,403,077 B1 | 6/2002 | Strom et al. |
| 6,548,653 B1 | 4/2003 | Young et al. |
| 6,586,398 B1 | 7/2003 | Kinstler et al. |
| 6,660,843 B1 | 12/2003 | Feige et al. |
| 6,750,334 B1 | 6/2004 | Gray et al. |
| 6,797,493 B2 | 9/2004 | Sun et al. |
| 6,808,902 B1 | 10/2004 | Treuheit et al. |
| 6,821,505 B2 | 11/2004 | Ward |
| 6,900,292 B2 | 5/2005 | Sun et al. |

(Continued)

FOREIGN PATENT DOCUMENTS

| | | |
|---|---|---|
| CA | 2045869 A1 | 12/1991 |
| CA | 2328490 A1 | 11/1999 |

(Continued)

OTHER PUBLICATIONS

Score, "Sequence 21 from U.S. Pat. No. 6,900,292," Accession No. AR670085, May 14, 2014. (2 pages).

Amoresano et al., "Structural characterization and independent folding of a chimeric glycoprotein comprising granulocyte-macrophage colony stimulating factor and erythropoietin sequences," *Glycobiology* 8(8):779-790, 1998.

Ashkenazi et al., "Immunoadhesins as research tools and therapeutic agents," *Current Opinion in Immunology* 9(2):195-200, 1997.

(Continued)

*Primary Examiner* — Elizabeth C. Kemmerer
*Assistant Examiner* — Regina M DeBerry
(74) *Attorney, Agent, or Firm* — Seed IP Law Group LLP

(57) ABSTRACT

A recombinant fusion protein comprising a human erythropoietin peptide portion linked to an immunoglobulin peptide portion is described. The fusion protein has a prolonged half-life in vivo in comparison to naturally occurring or recombinant native human erythropoietin. In one embodiment of the invention, the protein has a half-life in vivo at least three fold higher than native human erythropoietin. The fusion protein also exhibits enhanced erythropoietic bioactivity in comparison to native human erythropoietin. In one embodiment, the fusion protein comprises the complete peptide sequence of a human erythropoietin (EPO) molecule and the peptide sequence of an Fc fragment of human immunoglobulin IgG1. The Fc fragment in the fusion protein includes the hinge region, CH2 and CH3 domains of human immunoglobulin IgG1. The EPO molecule may be linked directly to the Fc fragment to avoid extraneous peptide linkers and lessen the risk of an immunogenic response when administered in vivo. In one embodiment the hinge region is a human Fc fragment variant having a non-cysteine residue at amino acid 6. The invention also relates to nucleic acid and amino acid sequences encoding the fusion protein and transfected cell lines and methods for producing the fusion protein. The invention further includes pharmaceutical compositions comprising the fusion protein and methods of using the fusion protein and/or the pharmaceutical compositions, for example to stimulate erythropoiesis in subjects in need of therapy.

20 Claims, 16 Drawing Sheets

Specification includes a Sequence Listing.

(56) References Cited

U.S. PATENT DOCUMENTS

| | | | |
|---|---|---|---|
| 6,936,439 | B2 | 8/2005 | Mann et al. |
| 6,987,006 | B2 | 1/2006 | Fleer et al. |
| 6,989,365 | B2 | 1/2006 | Fleer et al. |
| 7,030,226 | B2 | 4/2006 | Sun et al. |
| 7,041,478 | B2 | 5/2006 | Fleer et al. |
| 7,056,701 | B2 | 6/2006 | Fleer et al. |
| 7,250,493 | B2 | 7/2007 | Sun et al. |
| 7,253,264 | B1 | 8/2007 | Lauffer et al. |
| 7,625,564 | B2 | 12/2009 | Wang et al. |
| 8,067,548 | B2 | 11/2011 | Wang et al. |
| 8,431,132 | B2 | 4/2013 | Wang et al. |
| 9,375,487 | B2 | 6/2016 | Wang et al. |
| 2003/0044423 | A1 | 3/2003 | Gillies et al. |
| 2003/0235536 | A1 | 12/2003 | Blumberg et al. |
| 2004/0063912 | A1 | 4/2004 | Blumberg et al. |
| 2004/0175824 | A1 | 4/2004 | Sun et al. |
| 2004/0127682 | A1 | 7/2004 | Neville et al. |
| 2005/0048572 | A1 | 3/2005 | Reilly et al. |
| 2005/0124045 | A1 | 6/2005 | Sun et al. |
| 2005/0202538 | A1 | 9/2005 | Gillies et al. |
| 2005/0238646 | A1 | 10/2005 | Ledbetter et al. |
| 2005/0260194 | A1 | 11/2005 | Peters et al. |
| 2006/0025573 | A1 | 2/2006 | Gillies et al. |
| 2006/0134105 | A1 | 6/2006 | Lazar et al. |
| 2007/0065440 | A1 | 3/2007 | Tomlinson et al. |
| 2007/0178112 | A1 | 8/2007 | Wang et al. |
| 2007/0269371 | A1 | 11/2007 | Krummen et al. |
| 2008/0260746 | A1 | 10/2008 | Abderrahim et al. |
| 2009/0297522 | A1 | 12/2009 | Wang et al. |
| 2010/0098716 | A1 | 4/2010 | Wang et al. |
| 2010/0099145 | A1 | 4/2010 | Wang et al. |
| 2012/0100099 | A1 | 4/2012 | Wang et al. |

FOREIGN PATENT DOCUMENTS

| | | |
|---|---|---|
| EP | 0 464 533 A1 | 1/1992 |
| WO | 99/02709 A1 | 1/1999 |
| WO | 99/58662 A1 | 11/1999 |
| WO | 99/66054 A2 | 12/1999 |
| WO | 01/03737 A1 | 1/2001 |
| WO | 01/30320 A1 | 5/2001 |
| WO | 01/36489 A2 | 5/2001 |
| WO | 01/76640 A2 | 10/2001 |
| WO | 01/81405 A2 | 11/2001 |
| WO | 02/48194 A1 | 6/2002 |
| WO | 02/056910 A1 | 7/2002 |
| WO | 02/072605 A2 | 9/2002 |
| WO | 03/046013 A1 | 6/2003 |
| WO | 03/048210 A1 | 6/2003 |
| WO | 2004/004798 A2 | 1/2004 |
| WO | 2004/101739 A2 | 11/2004 |
| WO | 2005/001025 A2 | 1/2005 |
| WO | 2005/063808 A1 | 7/2005 |
| WO | 2005/079232 A2 | 9/2005 |
| WO | 2005/100395 A2 | 10/2005 |
| WO | 2006/079169 A1 | 8/2006 |
| WO | 2007/085084 A1 | 8/2007 |

OTHER PUBLICATIONS

Bitonti et al., "Pulmonary delivery of an erythropoietin Fc fusion protein in non-human primates through an immunoglobulin transport pathway," *Proc. Natl. Acad. Sci. U.S.A.* 101(26):9763-9768, 2004.
Brekke et al., "Structure-Function Relationships of Human IgG," *The Immunologist* 2:125-130, 1994.
Brekke et al., "The structural requirements for complement activation by IgG: does it hinge on the hinge?" *Immunology Today* 16(2):85-89, 1995.
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.* 111(5 Pt. 1):2129-2138, 1990.
Chica et al., "Semi-rational approaches to engineering enzyme activity: combining the benefits of directed evolution and rational design," *Current Opinion in Biotechnology* 16(4):378-384, 2005.
Coscarella et al., "Pharmacokinetic and immunogenic behavior of three recombinant human GM-CSF-EPO hybrid proteins in cynomolgus monkeys," *Mol. Biotechnol.* 10(2): 115-122, 1998.
Coscarella et al., "Production of recombinant human GM-CSF-EPO hybrid proteins: in vitro biological characterization," *Eur. J. Haematol.* 59(4):238-246, 1997.
Dalle et al., "Dimeric erythropoietin fusion protein with enhanced erythropoietic activity in vitro and in vivo," *Blood* 97(12):3776-3782, 2001.
Dumont et al., "Delivery of an erythropoietin-Fc fusion protein by inhalation in humans through an immunoglobulin transport pathway," *J. Aerosol. Med.* 18 (3):294-303, 2005.
Final Rejection, dated Feb. 25, 2011, for U.S. Appl. No. 12/180,455, 1 pages.
Genbank, "Sequence 21 from patent U.S. Pat. No. 6,900,292," Accession No. AR670085.1, Jun. 13, 2005, 1 page.
Lazar et al., "Transforming growth factor alpha: mutation of aspartic acid 47 and leucine 48 results in different biological activities," *Mol. Cell Biol.* 8(3): 1247-1252, 1988.
Lee et al., "The prolonged half-lives of new erythropoietin derivatives via peptide addition," *Biochem. Biophys. Res. Commun.* 339(1):380-385, 2006.
Martin et al., "Crystal Structure at 2.8 Å of an FcRn/Heterodimeric Fc Complex: Mechanism of pH-Dependent Binding," *Molecular Cell* 7:867-877, 2001.
Non-Final Rejection, dated Aug. 3, 2010, for U.S. Appl. No. 12/180,455, 10 pages.
Non-Final Rejection, dated Jul. 10, 2008, for U.S. Appl. No. 11/340,661, 10 pages.
Non-Final Rejection, dated Jul. 22, 2009, for U.S. Appl. No. 11/340,661, 5 pages.
Non-Final Rejection, dated Mar. 5, 2009, for U.S. Appl. No. 11/340,661, 10 pages.
Non-Final Rejection, dated May 14, 2010, for U.S. Appl. No. 12/555,742, 7 pages.
Non-Final Rejection, dated Oct. 15, 2009, for U.S. Appl. No. 12/180,455, 16 pages.
Notice of Allowance and Fees Due, dated Feb. 14, 2011, for U.S. Appl. No. 12/555,742, 6 pages.
Notice of Allowance and Fees Due, dated Jul. 25, 2011, for U.S. Appl. No. 12/180,455, 5 pages.
Notice of Allowance and Fees Due, dated Oct. 11, 2011, for U.S. Appl. No. 12/555,743, 7 pages.
Notice of Allowance and Fees Due, dated Aug. 13, 2009, for U.S. Appl. No. 11/340,661, 2 pages.
Restriction Requirement, dated Jun. 16, 2009, for U.S. Appl. No. 12/180,455, 8 pages.
Restriction Requirement, dated Mar. 17, 2008, for U.S. Appl. No. 11/340,661, 5 pages.
Restriction Requirement, dated Mar. 7, 2011, for U.S. Appl. No. 12/555,743, 6 pages.
Roopenian et al., "FcRn: the neonatal Fc receptor comes of age," *Nature Reviews* 7:715-725, 2007.
Schriebl et al., "Biochemical characterization of rhEpo-Fc fusion protein expressed in CHO cells," *Protein Expr. Purif.* 49(2):265-275, 2006.
Sen et al., "Developments in directed evolution for improving enzyme functions," *Appl. Biochem. Biotechnol.* 143(3):212-223, 2007.
Singh et al., "Protein Engineering Approaches in the Post-Genomic Era," *Current Protein and Peptide Science* 18:1-11,2017.
Skolnick et al., "From genes to protein structure and function: novel applications of computational approaches in the genomic era," *Trends Biotechnol.* 18(1):34-39, 2000.
Su et al., "High-level expression of human stem cell factor fused with erythropoietin mimetic peptide in *Escherichia coli*," *Protein Expr. Purif.* 47(2):477-482, 2006.

(56) References Cited

OTHER PUBLICATIONS

Sytkowski et al., "An erythropoietin fusion protein comprised of identical repeating domains exhibits enhanced biological properties," *J. Biol. Chem.* 274(35):24773-24778, 1999.

Wang et al., "Fusion Proteins Having Mutated Immunoglobulin Hinge Region," U.S. Appl. No. 12/180,455, filed Jul. 25, 2008, 65 pages.

Way et al., "Improvement of Fc-erythropoietin structure and pharmacokinetics by modification at a disulfide bond," *Protein Eng. Des. Sel.* 18(3):111-118, 2005.

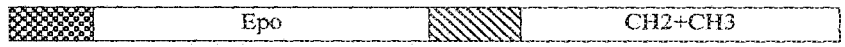

Signal peptide                  Hinge

FIG. 1A

```
ATGGGGGTGCACGAATGTCCTGCCTGGCTGTGGCTTCTCCTGTCCCTGCTGTCGCTCCCT    60
 M  G  V  H  E  C  P  A  W  L  W  L  L  L  S  L  L  S  L  P
CTGGGCCTCCCAGTCCTGGGCGCCCCACCACGCCTCATCTGTGACAGCCGAGTCCTGGAG   120
 L  G  L  P  V  L  G  A  P  P  R  L  I  C  D  S  R  V  L  E
AGGTACCTCTTGGAGGCCAAGGAGGCCGAGAATATCACGACGGGCTGTGCTGAACACTGC   180
 R  Y  L  L  E  A  K  E  A  E  N  I  T  T  G  C  A  E  H  C
AGCTTGAATGAGAATATCACTGTCCCAGACACCAAAGTTAATTTCTATGCCTGGAAGAGG   240
 S  L  N  E  N  I  T  V  P  D  T  K  V  N  F  Y  A  W  K  R
ATGGAGGTCGGGCAGCAGGCCGTAGAAGTCTGGCAGGGCCTGGCCCTGCTGTCGGAAGCT   300
 M  E  V  G  Q  Q  A  V  E  V  W  Q  G  L  A  L  L  S  E  A
GTCCTGCGGGGCCAGGCCCTGTTGGTCAACTCTTCCCAGCCGTGGGAGCCCCTGCAGCTG   360
 V  L  R  G  Q  A  L  L  V  N  S  S  Q  P  W  E  P  L  Q  L
CATGTGGATAAAGCCGTCAGTGGCCTTCGCAGCCTCACCACTCTGCTTCGGGCTCTGCGA   420
 H  V  D  K  A  V  S  G  L  R  S  L  T  T  L  L  R  A  L  R
GCCCAGAAGGAAGCCATCTCCCCTCCAGATGCGGCCTCAGCTGCTCCACTCCGAACAATC   480
 A  Q  K  E  A  I  S  P  P  D  A  A  S  A  A  P  L  R  T  I
ACTGCTGACACTTTCCGCAAACTCTTCCGAGTCTACTCCAATTTCCTCCGGGGAAAGCTG   540
 T  A  D  T  F  R  K  L  F  R  V  Y  S  N  F  L  R  G  K  L
AAGCTGTACACAGGGGAGGCCTGCAGGACAGGGGACAGAGTTGAGCCCAAATCTGGTGAC   600
 K  L  Y  T  G  E  A  C  R  T  G  D  R  V  E  P  K  S  G  D
AAAACTAGTACATGCCCACCGTGCCCAGCACCTGAACTCCTGGGGGGACCGTCAGTCTTC   660
 K  T  S  T  C  P  P  C  P  A  P  E  L  L  G  G  P  S  V  F
CTCTTCCCCCCAAAACCCAAGGACACCCTCATGATCTCCCGGACCCCTGAGGTCACATGC   720
 L  F  P  P  K  P  K  D  T  L  M  I  S  R  T  P  E  V  T  C
GTGGTGGTGGACGTGAGCCACGAAGACCCTGAGGTCAAGTTCAACTGGTACGTGGACGGC   780
 V  V  V  D  V  S  H  E  D  P  E  V  K  F  N  W  Y  V  D  G
GTGGAGGTGCATAATGCCAAGACAAAGCCGCGGGAGGAGCAGTACAACAGCACGTACCGT   840
 V  E  V  H  N  A  K  T  K  P  R  E  E  Q  Y  N  S  T  Y  R
GTGGTCAGCGTCCTCACCGTCCTGCACCAGGACTGGCTGAATGGCAAGGAGTACAAGTGC   900
 V  V  S  V  L  T  V  L  H  Q  D  W  L  N  G  K  E  Y  K  C
AAGGTCTCCAACAAAGCCCTCCCAGCCCCCATCGAGAAAACCATCTCCAAAGCCAAAGGG   960
 K  V  S  N  K  A  L  P  A  P  I  E  K  T  I  S  K  A  K  G
CAGCCCCGAGAACCACAGGTGTACACCCTGCCCCCATCCCGGGATGAGCTGACCAAGAAC  1020
 Q  P  R  E  P  Q  V  Y  T  L  P  P  S  R  D  E  L  T  K  N
CAGGTCAGCCTGACCTGCCTGGTCAAAGGCTTCTATCCCAGCGACATCGCCGTGGAGTGG  1080
 Q  V  S  L  T  C  L  V  K  G  F  Y  P  S  D  I  A  V  E  W
GAGAGCAATGGGCAGCCGGAGAACAACTACAAGACCACGCCTCCCGTGCTGGACTCCGAC  1140
 E  S  N  G  Q  P  E  N  N  Y  K  T  T  P  P  V  L  D  S  D
GGCCCCTTCTTCCTCTACAGCAAGCTCACCGTGGACAAGAGCAGGTGGCAGCAGGGGAAC  1200
 G  P  F  F  L  Y  S  K  L  T  V  D  K  S  R  W  Q  Q  G  N
GTCTTCTCATGCTCCGTGATGCATGAGGCTCTGCACAACCACTACACGCAGAAGAGCCTC  1260
 V  F  S  C  S  V  M  H  E  A  L  H  N  H  Y  T  Q  K  S  L
TCCCTGTCTCCGGGTAAATAA                                         1320
 S  L  S  P  G  K  *
```

FIG. 1B

```
ATGGGGGTGCACGAATGTCCTGCCTGGCTGTGGCTTCTCCTGTCCCTGCTGTCGCTCCCT    60
 M  G  V  H  E  C  P  A  W  L  W  L  L  L  S  L  L  S  L  P
CTGGGCCTCCCAGTCCTGGGCGCCCCACCACGCCTCATCTGTGACAGCCGAGTCCTGGAG   120
 L  G  L  P  V  L  G  A  P  P  R  L  I  C  D  S  R  V  L  E
AGGTACCTCTTGGAGGCCAAGGAGGCCGAGAATATCACGACGGGCTGTGCTGAACACTGC   180
 R  Y  L  L  E  A  K  E  A  E  N  I  T  T  G  C  A  E  H  C
AGCTTGAATGAGAATATCACTGTCCCAGACACCAAAGTTAATTTCTATGCCTGGAAGAGG   240
 S  L  N  E  N  I  T  V  P  D  T  K  V  N  F  Y  A  W  K  R
ATGGAGGTCGGGCAGCAGGCCGTAGAAGTCTGGCAGGGCCTGGCCCTGCTGTCGGAAGCT   300
 M  E  V  G  Q  Q  A  V  E  V  W  Q  G  L  A  L  L  S  E  A
GTCCTGCGGGGCCAGGCCCTGTTGGTCAACTCTTCCCAGCCGTGGGAGCCCCTGCAGCTG   360
 V  L  R  G  Q  A  L  L  V  N  S  S  Q  P  W  E  P  L  Q  L
CATGTGGATAAAGCCGTCAGTGGCCTTCGCAGCCTCACCACTCTGCTTCGGGCTCTGCGA   420
 H  V  D  K  A  V  S  G  L  R  S  L  T  T  L  L  R  A  L  R
GCCCAGAAGGAAGCCATCTCCCCTCCAGATGCGGCCTCAGCTGCTCCACTCCGAACAATC   480
 A  Q  K  E  A  I  S  P  P  D  A  A  S  A  A  P  L  R  T  I
ACTGCTGACACTTTCCGCAAACTCTTCCGAGTCTACTCCAATTTCCTCCGGGGAAAGCTG   540
 T  A  D  T  F  R  K  L  F  R  V  Y  S  N  F  L  R  G  K  L
AAGCTGTACACAGGGGAGGCCTGCAGGACAGGGGACAGAGTTGAGCCCAAATCTTGTGAC   600
 K  L  Y  T  G  E  A  C  R  T  G  D  R  V  E  P  K  S  C  D
AAAAACTAGTACATGCCCACCGTGCCCAGCACCTGAACTCCTGGGGGGACCGTCAGTCTTC   660
 K  T  S  T  *  P  P  C  P  A  P  E  L  L  G  G  P  S  V  F
CTCTTCCCCCCAAAACCCAAGGACACCCTCATGATCTCCCGGACCCCTGAGGTCACATGC   720
 L  F  P  P  K  P  K  D  T  L  M  I  S  R  T  P  E  V  T  C
GTGGTGGTGGACGTGAGCCACGAAGACCCTGAGGTCAAGTTCAACTGGTACGTGGACGGC   780
 V  V  V  D  V  S  H  E  D  P  E  V  K  F  N  W  Y  V  D  G
GTGGAGGTGCATAATGCCAAGACAAAGCCGCGGGAGGAGCAGTACAACAGCACGTACCGT   840
 V  E  V  H  N  A  K  T  K  P  R  E  E  Q  Y  N  S  T  Y  R
GTGGTCAGCGTCCTCACCGTCCTGCACCAGGACTGGCTGAATGGCAAGGAGTACAAGTGC   900
 V  V  S  V  L  T  V  L  H  Q  D  W  L  N  G  K  E  Y  K  C
AAGGTCTCCAACAAAGCCCTCCCAGCCCCCATCGAGAAAACCATCTCCAAAGCCAAAGGG   960
 K  V  S  N  K  A  L  P  A  P  I  E  K  T  I  S  K  A  K  G
CAGCCCCGAGAACCACAGGTGTACACCCTGCCCCCATCCCGGGATGAGCTGACCAAGAAC  1020
 Q  P  R  E  P  Q  V  Y  T  L  P  P  S  R  D  E  L  T  K  N
CAGGTCAGCCTGACCTGCCTGGTCAAAGGCTTCTATCCCAGCGACATCGCCGTGGAGTGG  1080
 Q  V  S  L  T  C  L  V  K  G  F  Y  P  S  D  I  A  V  E  W
GAGAGCAATGGGCAGCCGGAGAACAACTACAAGACCACGCCTCCCGTGCTGGACTCCGAC  1140
 E  S  N  G  Q  P  E  N  N  Y  K  T  T  P  P  V  L  D  S  D
GGCCCCTTCTTCCTCTACAGCAAGCTCACCGTGGACAAGAGCAGGTGGCAGCAGGGGAAC  1200
 G  P  F  F  L  Y  S  K  L  T  V  D  K  S  R  W  Q  Q  G  N
GTCTTCTCATGCTCCGTGATGCATGAGGCTCTGCACAACCACTACACGCAGAAGAGCCTC  1260
 V  F  S  C  S  V  M  H  E  A  L  H  N  H  Y  T  Q  K  S  L
TCCCTGTCTCCGGGTAAATAA                                         1320
 S  L  S  P  G  K  *
```

*FIG. 12*

RECOMBINANT HUMAN EPO-FC FUSION PROTEINS WITH PROLONGED HALF-LIFE AND ENHANCED ERYTHROPOIETIC ACTIVITY IN VIVO

RELATED APPLICATION

This application is a continuation of U.S. non-provisional application Ser. No. 12/162,320 filed Dec. 10, 2008, now allowed, which is a 371 application of PCT/CA2007/000107 filed Jan. 25, 2007, which is a continuation-in-part of U.S. patent application Ser. No. 11/340,661 filed Jan. 27, 2006, now U.S. Pat. No. 7,625,564, each of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 700171_402C1_SEQUENCE_LISTING.txt. The text file is 21.5 KB, was created on Nov. 14, 2018, and is being submitted electronically via EFS-Web.

TECHNICAL FIELD

This application relates to human erythropoietin fusion proteins.

BACKGROUND

Human erythropoietin (EPO), a member of the haematopoietic growth factor family, is synthesized mainly in the adult kidney and fetal liver in response to tissue hypoxia due to decreased blood oxygen availability [1]. The principal function of EPO is to act directly on certain red blood cell (RBC) progenitors and precursors in the bone marrow to stimulate the synthesis of hemoglobin and mature RBCs. It also controls the proliferation, differentiation, and maturation of RBCs. Recombinant EPO having the amino-acid sequence of naturally occurring EPO has been produced and approved to treat anemia associated with kidney functional failure, cancer and other pathological conditions [2]. In addition to its erythropoietic properties, recent research reports [3] indicate that EPO also acts on non-bone marrow cells such as neurons, suggesting other possible physiological/pathological functions of EPO in the central nervous system (CNS) and other organs/systems. Since EPO receptors have been found in many different organs, EPO may have multiple biological effects, such as acting as an anti-apoptotic agent.

Human EPO is a glycoprotein with a molecular weight of 30.4 kilodaltons. Carbohydrates account for approximately 39% of its total mass. The EPO gene is located on chromosome 7q11-22 and spans a 5.4 kb region with five exons and four introns [4]. The precursor of EPO consists of 193 amino acids. Cleavage of the leader sequence and the last amino acid Arg by post-translational modification yields the mature EPO having 165 amino acids. Glycosylation, with three N-linked sites at Asn 24, Asn38, Asn83 and one O-linked site at Ser126, plays a crucial role in the biosynthesis, tertiary structure and the in vivo bioactivity of EPO [5]. EPO functions by binding to an erythropoietin receptor, a glycosylated and phosphorylated transmembrane polypeptide with the molecular weight of 72-78 kilodaltons. This binding triggers the homodimerization of the receptors that leads to the activation of several signal transduction pathways: JAK2/STATS system, G-protein, calcium channel, and kinases. Two molecules of EPO protein are needed to bind simultaneously to one receptor molecule to achieve optimal receptor activation [6].

As the first hematopoietic growth factor approved for human therapy, recombinant human EPO (rHuEPO) has been used for the treatment of anemia resulting from chronic renal failure, cancers (primarily chemotherapy-associated anemia), autoimmune diseases, AIDS, surgery, bone marrow transplantation and myelodysplastic syndromes, etc. Interestingly, recent studies have also observed that rHuEPO has non-blood system functions and shows the potential of being used as a neuroprotective drug for cerebral ischemia, brain trauma, inflammatory disease and neural degenerative disorders [7].

Currently, three kinds of rHuEPO or rHuEPO analogs are commercially available, namely rHuEPO alpha, rHuEPO beta, and darbepoetin alfa [8]. These three recombinant proteins bind to the same erythropoietin receptor, but differ in structure, degree of glycosylation, receptor-binding affinity and in vivo metabolism. Since the initial introduction of rHuEPO-alpha in the 1980s, clinicians quickly recognized the frequent dose/injection requirement of the drug as a significant shortcoming. The mean in vivo half-lives of rHuEPO alpha and rHuEPO beta administered intravenously or subcutaneously are only 8.5 and 17 hours respectively [9, 10]. Patients therefore need an injection schedule of daily, twice weekly or three times per week which imposes a burden on both patients and health care providers. Thus, there has been a longstanding need to develop recombinant EPO analogs having a longer in vivo half-life and/or enhanced erythropoietic activity.

Attempts have been made in the prior art to genetically change or chemically modify the structure of the native EPO protein to either slow down its in vivo metabolism or improve its therapeutic properties. For example, there appears to be a direct correlation between the amounts of sialic acid-containing carbohydrates on the EPO molecule and its in vivo metabolism and functional activity. Increasing the carbohydrate content of the EPO molecule thus results in a longer half-life and enhanced activities in vivo [11, 12]. Amgen has designed the rHuEPO analog darbepoetin alpha to include 5 N-linked carbohydrate chains, two more than rHuEPO. Darbepoetin alpha is also known as Novel Erythropoiesis Stimulating Protein (NESP) and is sold under the trademark ARANESP™. Darbepoetin alpha differs from native human EPO at five positions (Ala30Asn, His32Thr, Pro87Val, Trp88Asn, Pro90Thr) which allows for the attachment of two additional N-linked oligosaccharides at asparagines residue positions 30 and 88. Darbepoetin alpha binds to the EPO receptor in an identical manner as native EPO to induce intracellular signaling involving tyrosine phosphorylation by JAK-2 kinase and the same intracellular molecules Ras/MAP-k, P13-k and STAT-5. Due to the increased carbohydrate content, the half-life of darbepoetin alpha in both animals and humans is almost three fold-longer than that of rHuEPO-alpha (25.3 hours vs 8.5 hours) [9]. Darbepoetin alpha (ARANESP™) also appears to exhibit enhanced bioactivity in comparison to naturally occurring or recombinant human EPO in vivo [13] and has been approved by FDA as a second generation rHuEPO drug; this drug only needs to be administrated once per week to achieve the identical therapeutic effects of 2-3 time injections per week of rHuEPO[10, 14, 15].

Other attempts to extend the half-life of EPO have focused on increasing the molecular weight of the EPO protein through chemical conjugation with polyethylene glycol (PEGylation) and the like. PEGylated-EPO has a much larger molecular weight and is protected from being cleared from circulation and therefore has a longer plasma half-life [16]. However, PEGylation may alter the protein structure resulting in unanticipated changes of function and specificity of the EPO moiety. There are also reports of increasing the molecular weight of EPO by other methods, such as to link the EPO molecule to a carrier protein (human albumin), or to form the homodimerization of two complete EPO molecules by using linking peptides (3- to 17-amino acids) or by chemical cross-linking reagents [17, 18, 19, 20]. While all these methods have achieved some success in extending the half-life and enhancing the activities of EPO, combining the EPO molecule with the Fc fragment of human immunoglobulin (IgG) in a fusion protein as described in the present application achieves unique advantages.

Human immunoglobulin IgG is composed of four polypeptides linked covalently by disulfide bonds (two identical copies of light chain and heavy chain). The proteolysis of IgG molecule by papain generates two Fab fragments and one Fc fragment. The Fc fragment consists of two polypeptides linked together by disulfide bonds. Each polypeptide, from N- to C-terminal, is composed of a hinge region, a CH2 domain and a CH3 domain. The Fc fragment structure is almost the same among all subtypes of human immunoglobulin. IgG is among one of the most abundant proteins in the human blood and makes up 70 to 75% of the total immunoglobulins in human serum. The half-life of IgG in circulation is the longest among all five types of immunoglobulin and may reach 21 days.

Modern bio-engineering technology has been successfully applied to the creation of fusion proteins consisting of therapeutic protein fragments, such as cytokines and soluble receptors, and the Fc fragment of human IgG [21, 22, 23, 24]. These fusion proteins have a significantly longer in vivo half-life while retaining their biological and therapeutic properties. So far two fusion proteins comprising an Fc fragment have been successfully developed as biomedicines and approved by FDA for the treatment of rheumatoid arthritis and chronic plaque psoriasis [25, 26].

It has been shown in the prior art that dimers of two EPO molecules linked either by chemical cross-linking or by a polypeptide exhibit enhanced in vivo activities and a prolonged half-life [17, 19]. The enhanced activity may due to the more efficient binding of the EPO dimer to one receptor, and the prolonged in vivo half-life due to the larger size of the dimer protein. However, the chemical cross-linking process is not efficient and is difficult to control. Moreover, the linkage peptide in the dimer of EPO may alter the three-dimensional structure of EPO molecule and the peptide itself may stimulate immunogenic responses in vivo. These shortcomings impair the therapeutic potential of EPO dimers, particularly since EPO replacement therapy in renal patients is life-long.

The need has therefore arisen for EPO analogs that have a significantly longer half-life and enhanced erythropoietic activities in vivo but have no increased immunogenic properties.

SUMMARY OF THE INVENTION

In accordance with the invention, a recombinant fusion protein comprising a human erythropoietin peptide portion linked to an immunoglobulin peptide portion is described. The fusion protein has a prolonged half-life in vivo in comparison to naturally occurring or recombinant native human erythropoietin. In one embodiment of the invention, the protein has a half-life in vivo at least three fold higher than native human erythropoietin. The fusion protein may also exhibit enhanced erythropoietic bioactivity in comparison to native human erythropoietin.

In one embodiment of the invention the immunoglobulin peptide portion is an Fc fragment, such as an IgG1 fragment. The Fc fragment includes CH2 and CH3 domains and a hinge region. The EPO peptide portion may be directly linked to the hinge region. Preferably the hinge region is at least 9 amino acids in length. In one embodiment, the EPO peptide portion has a cysteine residue proximate the C terminal thereof and the hinge region includes a cysteine residue located nearest the EPO peptide portion. Preferably these two cysteine residues are spaced at least 12 amino acids apart. In one embodiment, the EPO peptide portion may comprise a complete EPO molecule directly linked to the immunoglobulin portion (i.e. no external peptide linkers are interposed between the EPO and immunoglobulin portions).

The invention also relates to multimeric protein constructs comprising multiple units of the fusion protein of the invention. For example, two fusion proteins may be assembled as a dimer, wherein the hinge regions of the proteins are joined by disulphide bonds. The dimer has the general shape of a IgG molecule and is more stable than free EPO molecules.

The invention also relates to nucleic acid and amino acid sequences encoding the fusion protein and transfected cell lines and methods for producing the fusion protein. The invention further includes pharmaceutical compositions comprising the fusion protein and methods of using the fusion protein and/or the pharmaceutical compositions, for example to stimulate erythropoiesis in subjects in need of therapy.

BRIEF DESCRIPTION OF THE DRAWINGS

In drawings which illustrate various embodiments of the invention but which are not intended to be construed in a limiting manner:

FIG. 1A is a schematic diagram showing the general structure of the recombinant human EPO-Fc fusion protein (rHuEPO-Fc) of the invention.

FIG. 1B is a sequence listing showing the nucleotide sequence (corresponding to SEQ ID NO:3) and the deduced amino-acid (aa) sequence (corresponding to SEQ ID NO:4) of rHuEPO-Fc protein. The total length of DNA is 1281 bp. The 426 amino acids in the deduced protein sequence include 27 aa for the signal peptide (SEQ ID NO:15) and 399 aa for the complete rHuEPO-Fc protein (SEQ ID NO:2). The complete rHuEPO-Fc protein consists of human EPO domain (166 aa, SEQ ID NO:16), hinge region (16 aa, underlined, SEQ ID NO:17), and CH2 and CH3 domains (217 aa, SEQ ID NO:18) of the Fc fragment of human IgG1. The calculated molecular weight of the polypeptide of the mature rHuEPO-Fc fusion protein is 44.6 kDa, composed of 18.5 kDa (41.4%) of EPO fragment and 26.1 kDa (58.6%) of IgG1 Fc fragment. A homodimer is formed by two disulfide bonds via the two cysteine residues (boxed) within the hinge region. At residue 172 of the mature fusion protein (i.e. the $6^{th}$ amino acid of hinge region (SEQ ID NO:17)) the native cysteine residue has been substituted by glycine (bold).

FIG. 4A: Mice treated with rHuEPO-Fc. FIG. 4B: Mice treated with native rHuEPO FIG. 5A: Mice treated with rHuEPO-Fc. FIG. 5B: Mice treated with native rHuEPO FIG. 6A: Mice with treatment once a week. FIG. 6B: Mice with treatment 3 times a week.

FIG. 10A: s.c. once every week. FIG. 10B: s.c. once every 2 weeks. FIG. 10C: i.v. once every two weeks.

FIG. 12 is a sequence listing showing the nucleotide sequence (corresponding to SEQ ID NO:11) and the deduced amino-acid (aa) sequence (corresponding to SEQ ID NO:12) of a wild type rHuEPO-FcC protein. The sequence particulars are the same as shown in FIG. 1B except that a native, wild type cysteine residue is present at residue 172 of the mature fusion protein (i.e. the $6^{th}$ amino acid of the hinge region).

DETAILED DESCRIPTION OF THE INVENTION

Figure 2:
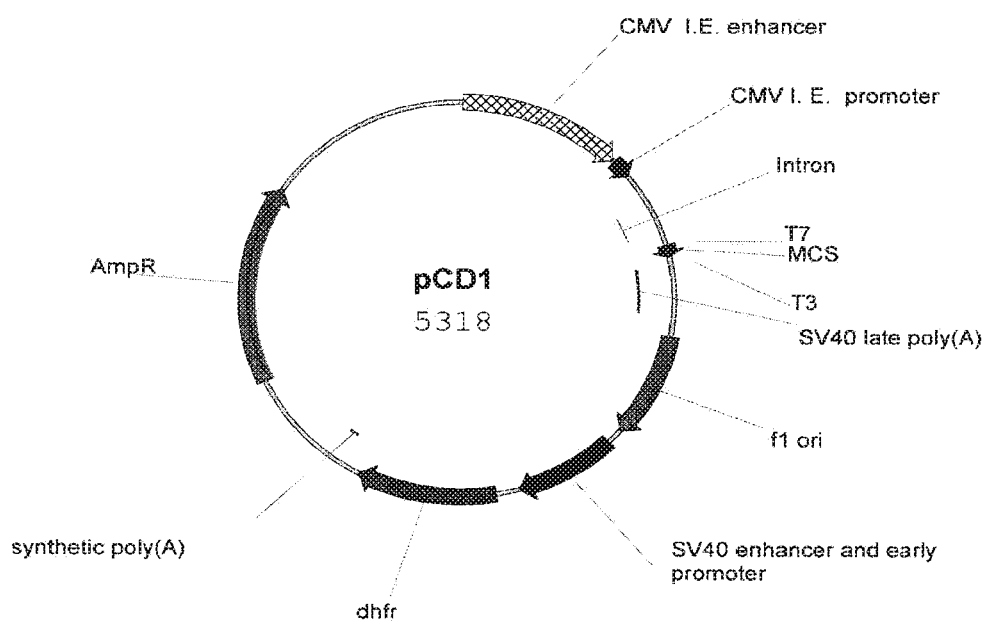
FIG. 2 is a schematic diagram showing the structure and features of the mammalian expression plasmid pCD1 used for inserting the DNA sequence encoding the polypeptide of the rHuEPO-Fc fusion protein, and for transfecting CHO cells that express the rHuEPO-Fc fusion protein.

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive sense.

This application relates to a novel fusion protein having erythropoietic properties. The fusion protein, referred to herein as rHuEPO-Fc, comprises a human erythropoietin (EPO) molecule recombinantly linked to an immunoglobulin Fc fragment. As discussed further below, the fusion protein may be in the form of a dimer consisting of two identical polypeptide subunits. In the embodiment shown schematically in FIG. 1A, each polypeptide subunit, from the N-terminal to C-terminal, consists of the polypeptide sequence of the human EPO molecule and the polypeptide sequence of the hinge region, CH2 domain and CH3 domain of the Fc fragment of human immunoglobulin IgG1. The two polypeptide subunits are connected together by disulfide bonds between the respective hinge regions to form the dimer structure. The dimer thus has the same general shape as an IgG molecule and exhibits better stability than free EPO molecules as discussed in the examples below.

As will be apparent to a person skilled in the art, the hinge region of an intact immunoglobulin provides the protein sufficient flexibility for effective antigen-antibody binding.

Similarly, in the present invention the hinge region is included in the design of the rHuEPO-Fc fusion protein to maintain its flexibility, especially when the fusion protein is in the dimer form. As described below, this allows the normal binding of the EPO portion of the rHuEPO-Fc fusion protein to EPO receptors to activate EPO biological functions. It is believed that the dimer form of the rHuEPO-FC fusion protein, by providing two EPO molecules, is capable of inducing the optimal activation of EPO receptors (for example, by facilitating receptor cross-linking).

As demonstrated in the examples set forth below, the rHuEPO-Fc fusion protein has been successfully synthesized using recombinant DNA techniques. The fusion protein has been shown in mice, rat and primate studies to exhibit a prolonged in vivo half-life and enhanced erythropoietic properties in comparison to naturally occurring or recombinant native human EPO. As used in this patent application, the terms "native human erythropoietin" and "native human EPO" mean EPO having an unmodified wild type structure. As will be appreciated by a person skilled in the art, native human EPO may be naturally occurring or recombinantly produced (e.g. rHuEPO alpha). The term "native human EPO" does not include rHuEPO analogs, such as darbepoetin alpha where the EPO structure has been significantly modified, such as by hyperglycosylation.

The nucleic acid sequence of the rHuEPO-Fc fusion protein of the present invention is shown in SEQ ID NO:1. The corresponding deduced amino acid sequence is shown in SEQ ID NO:2. The complete rHuEPO-Fc fusion protein is 399 amino acids in length. As shown in FIG. 1B, the complete rHuEPO-Fc fusion protein consists of the EPO domain (166 amino acids, SEQ ID NO:16), the hinge region (16 amino acids, underlined, SEQ ID NO:17) and the CH2 and CH3 domains (217 amino acids, SEQ ID NO:18). A signal or leader peptide sequence consisting of 27 amino acids (SEQ ID NO:15) is also shown in FIG. 1B. The signal peptide is cleaved during synthesis of rHuEPO-Fc. The nucleic and amino acid sequences of rHuEPO-Fc including the signal or leader peptide are shown in SEQ ID NO:3 and SEQ ID NO:4, respectively.

As shown best in FIG. 1B and SEQ ID NO:2, the EPO domain has a cysteine residue near the C-terminal thereof at amino acid number 161. The hinge region includes 2 cysteine residues, at amino acid numbers 178 and 181 which are boxed in FIG. 1B. The hinge region cysteine residues form the disulphide bonds between the polypeptide subunits of the homodimer as discussed above. The naturally occurring hinge region of a human IgG1 fragment also has a cysteine at residue number 6 of the hinge region portion (SEQ ID NO:17) (measured from the N-terminal). In the present invention, the cysteine residue 6 of the hinge portion has been substituted by a non-cysteine residue. In particular, in the embodiment of FIG. 1B and SEQ ID NO:2, the amino acid cysteine has been substituted by glycine (at amino acid residue 172 of rHuEPO-Fc, which corresponds to residue 6 of the hinge region (SEQ ID NO:17)). As will be apparent to a person skilled in the art, other non-cysteine residues could also be substituted for cysteine at this location to avoid formation of a disulphide bond.

As a result of the amino acid substitution at residue 172, the first cysteine residue of the hinge region (at residue 178) is spaced 17 amino acids from the above-described cysteine residue of the EPO domain (at residue 161). The inventors believe that the minimum spacing between the cysteine residue 161 of the EPO domain and the first cysteine residue of the hinge region should be at least 12 amino acids to enable successful assembly and/or EPO receptor binding of a homodimer of rHuEPO-Fc. That is, if residue 172 is a cysteine residue, an undesirable disulphide bond may potentially be formed, such as between cysteine residues 161 and 172. This may alter the three dimensional structure of the EPO molecule, resulting in biological inactivity or reduced biological activity.

In one embodiment of the invention, the EPO domain is linked directly to the Fc fragment portion of the fusion protein. By avoiding providing an external linker peptide, the preferred three dimensional structure of the rHuEPO-Fc fusion peptide is maintained and the risk of triggering an undesirable immunogenic response is minimized. The hinge region of the Fc fragment is preferably at least 9 amino acids in length and is preferably in the range of about 10-20 amino acids in length.

EXAMPLES

The following examples will further illustrate the invention in greater detail although it will be appreciated that the invention is not limited to the specific examples.

1. Construction of the Recombinant Plasmid pCdEpo-Fc Encoding the Fusion Protein of HuEPO-Fc.

The full length DNA molecule, which encodes the amino-acid sequence of the polypeptide of rHuEPO-Fc, was generated by overlapping PCR using the following oligo primers (QIAGEN Inc., US):

```
EF5:
5'-ccggaattcgccaccatgggggtgcacgaatgtcctgcct-3';

EF3:
5'-ttttccttttgcggccgcttatttacccggagacagggagag-3';

EFL5:
5'-aggcctgcaggacaggggacagagttgagcccaaatctggtgac
a-3';

EFL3:
5'-tgtcaccagatttgggctcaactctgtcccctgtcctgcaggcc
t-3'.
```

The sequences of the above-noted primers are listed in SEQ ID NO:5 to SEQ ID NO:8, respectively.

EcoR I and Not I sites were introduced in EF5 and EF3, respectively. For optimal expression of the HuEPO-Fc protein in mammalian cells, the Kozak sequence (GCCACCATGG), corresponding to SEQ ID NO:13, was also introduced in EF5. EFL5 and EFL3 are complementary sequences consisting of 3'-terminal DNA sequence of Epo (23 bp) and 5'-terminal DNA sequence of IgG1 hinge (22 bp).

First, an EPO DNA fragment of 0.6 kb was amplified by PCR (Platinum Taq DNA Polymerase High Fidelity) with primers EF5 and EFL3 from plasmid p9E containing the full length of human EPO cDNA, Fc fragment of 0.7 kb with primers EF3 and EFL5 from plasmid pD containing the full length of human IgG1 cDNA sequence, respectively (p9E and pD are from the inventors' own lab). The two fragments were then purified and mixed in equal amount. Using the mix as template, the full length rHuEPO-Fc DNA of 1.3 kb was amplified by primers EF5 and EF3. The purified 1.3 kb fragment was digested by EocR I and Not I (New England Biolab Inc. US) and then cloned into EcoR I/Not I-digested mammalian expression vector pCD1 (FIG. 2). The resulting recombinant vector was named pCdEpo-Fc and the inserted nucleic-acid sequence encoding the amino-acid sequence of the HuEPO-Fc protein was confirmed by DNA sequencing.

2. Establishment of rHuEPO-Fc Expression Cell Line

Chinese hamster ovary cell with dihydrofolate reductase (dhfr) deficiency (CHO/dhfr⁻, ATCC No. CRL-9096), which has been approved by FDA for biological substance production, was used as the host cell for rHuEPO-Fc expression.

The CHO-dhfr⁻ cells were transfected with the recombinant vector pCdEpo-Fc using Lipofectamine (Gibco, Cat. No:18292-037, USA). The supernatants from the culture of selected clones were assayed by ELISA (Roche, Cat. No:1-693 417, Canada) for EPO activity. Positive clones were further screened under increasing Methotrexate (MTX) pressures. One cell line with highest rHuEPO-Fc protein expression was selected as the rHuEPO-Fc-expressing CHO cell-line, and gradually adapted to serum-free media (CD CHO Medium, Gibco, Cat. No:10743-029, USA). This rHuEPO-Fc-expressing CHO cell-line was used for the production of rHuEPO-Fc protein.

3. Purification of rHuEPO-Fc Protein rHuEPO-Fc protein molecules contained in the supernatants collected from the serum-free media culturing the rHuEPO-Fc-expressing CHO cells were isolated at first by Protein A affinity chromatography (Amersham, Cat. No:17-0402-01, Canada). The isolated proteins were further purified by gel filtration in HiLoad ¹⁶⁄₆₀ Superdex 200 pg column (Amersham, Cat. No:17-1069-01, Canada). The purity of the rHuEPO-Fc protein was more than 98% as determined by electrophoresis.

4. Determination of the Sizes of the Pure rHuEPO-Fc Protein

Figure 3:
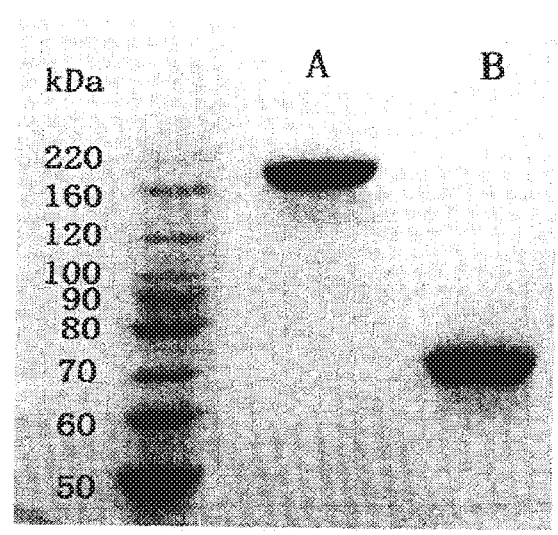
FIG. 3 is a SDS-PAGE image showing the sizes of the dimeric form of pure rHuEPO-Fc protein in non-reduced condition and monomeric form of pure rHuEPO-Fc protein in reduced condition by SDS-PAGE analysis. The purified rHuEPO-Fc protein from the supernatants of the cultured CHO cell-line expressing rHuEPO-FC exists mainly as the dimeric form and has a molecular weight of about 180 kDa on 8% Bis-Tris gel in non-reduced condition. In reduced condition (100 mM dithiothreitol, DTT) to break disulfide bonds, the dimer is separated into two identical monomeric units with a molecular weight of 75 kDa.

First, SDS-PAGE was carried out to determine the sizes of the pure rHuEPO-Fc protein. As shown in FIG. 3, a single band with molecular weight of about 180 kDa was seen on 8% Bis-Tris gel in the non-reduced condition, which measured the overall size of the protein with the existence of disulfide bonds. This indicated that most rHuEPO-Fc protein molecules were produced as the dimeric form, as expected from the design of the fusion protein. When SDS-PAGE analysis was conducted in the reducing condition (100 mM dithiothreitol, DTT) to break the disulfide bonds, only the band with molecular weight of 75 kDa was identified, consistent with the estimated molecular weight of single polypeptide chain of HuEPO-hinge region-CH2-CH3.

The accurate molecular weight of the pure rHuEPO-Fc fusion protein with glycosylation, determine by Mass Spectrum (MALDI-TOF-MS), was 111099 daltons (111.1 kDa). In this assay, only a single peak of protein was observed, indicating the purified rHuEPO-Fc protein was nearly 100% pure. The 15 amino acids of the N-terminal of the pure rHuEPO-Fc protein was determined by protein sequence analysis as: APPRLICDSRVLERY (corresponding to SEQ ID NO:14). This was consistent with the sequence of the first 15 amino acids of the native human EPO polypeptide, and confirms that the purified rHuEPO-Fc protein does have the right and complete EPO molecule sequence as predicted by the DNA sequence encoding the amino-acid sequences of the rHuEPO-Fc fusion protein.

5. Enhanced Erythropoietic Activities of rHuEPO-Fc in Normal Mice

In vivo experiments in mice were conducted to confirm the retaining of the erythropoietic activity of the rHuEPO-Fc protein and determine its efficacy compared to rHuEPO and darbepoetin-alpha. For comparison purpose, all the doses of three EPOs used in the described animal experiments of the invention: our rHuEPO-Fc, rHuEPO (i.e. native human EPO) and darbepoetin-alpha, were the amounts of EPO molecule portion alone based on the molar basis. In respect to rHuEPO-Fc protein, the EPO portion contributes to 41.4% of the total rHuEPO-Fc molecular weight as calculated by the ratio of the weight of amino acids of EPO in the weight of the total amino acids of the whole rHuEPO-Fc molecule (166 aa among 399 aa). The EPO amount for rHuEPO-Fc was then decided as 41.4% of the total amount of the rHuEPO-Fc protein.

rHuEPO-Fc (stock concentration: 0.5 mg/ml, purity of 98.6%) and native human rHuEPO (i.e. with natural human EPO structure) (6000 IU/0.5 ml, manufactured by Kirin Brewery Co., Japan) were diluted in carrier solution (2.5 mg/ml of human serum albumin, 5.8 mg/ml of sodium citrate, 0.06 mg/ml of citric acid and 5.8 mg/ml of sodium chloride, pH 5.5-5.6). The dose of rHuEPO in amount was calculated according to its activity/amount ration. BALB/c mice (6- to 8-week old, weighing 18-22 g, equal numbers of male and female, purchased from Experiment Animal Center, AMMS, China) were grouped randomly with 6 in each group. Each group of mice was treated with one combination of one dose (0.1, 0.5, 2.5, 12.5, 62.5 µg/kg), one injection route (i.v. through the tail vein or s. c.) and one injection schedule (three times per week or once per week). The control group of mice was injected with the equal volume of carrier solution. The treatment lasted for 3 weeks and the total observation times were 5 weeks. Peripheral blood samples (tail vein) for measurement were taken before treatment, on the $4^{th}$ day and $7^{th}$ day of every week for 5 weeks. Hb was measured as the index by absorptiometry. Mean±SD was calculated from the data of each group and t test was conducted among different groups.

Figure 4A:
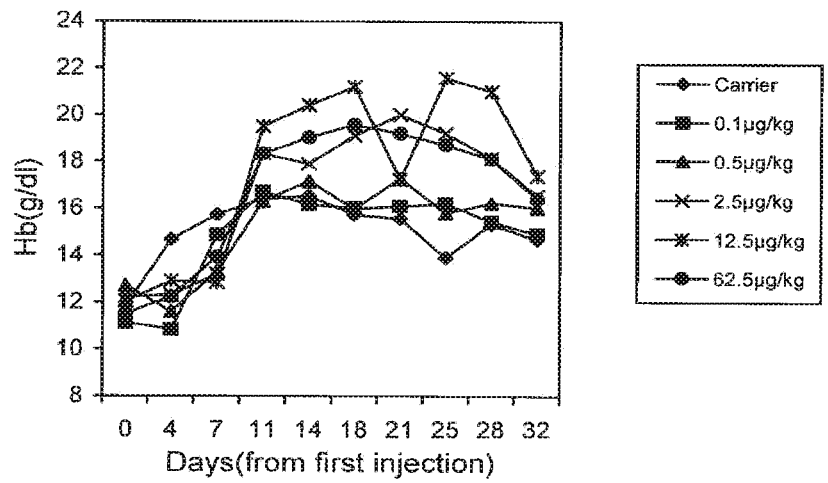
FIGS. 4A and 4B are graphs showing the dose-dependent increase of hemoglobin (Hb) levels in normal mice treated with three times per week subcutaneous injection (s.c.) of rHuEPO-Fc or rHuEPO. Each point represents the mean Hb level of the group (6 mice). Day 0 levels represent the Hb levels before treatment.
Figure 4B:
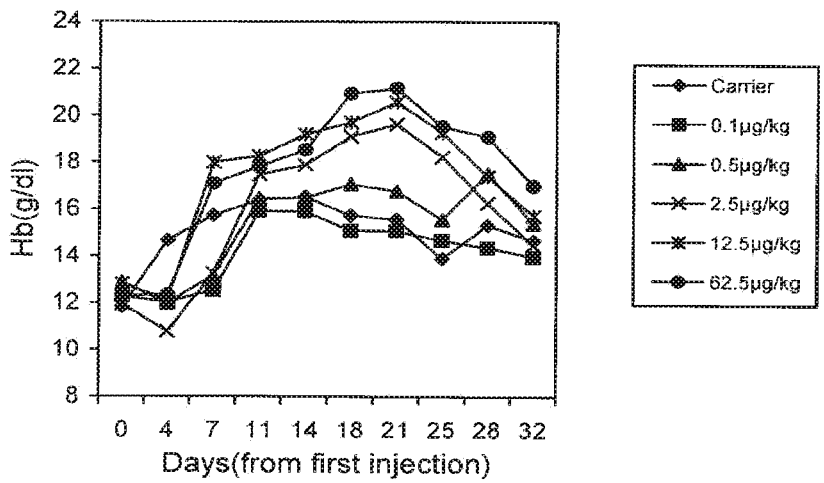

The administration of EPO three times per week to mice, provided that the EPOs have normal erythropoietic activity, would induce saturated stimulation of erythropoiesis. As shown in FIG. 4, both groups treated with 3 times per week s.c. had significant elevation of Hb levels even at the dose of 2.5 µg/kg. This experiment demonstrated that rHuEPO-Fc exhibited an in vivo erythropoietic activity as effective as rHuEPO. The elevation of Hb levels in the treated group was dose-dependent. However, saturated elevation of the Hb levels was induced in mice at the dose of 12.5 µg/kg of rHuEPO-Fc, whereas the similar saturated elevation of the Hb levels was only achieved at the dose of 62.5 µg/kg of rHuEPO. The elevation of Hb levels induced by 2.5 µg/kg of rHuEPO-Fc was also greater than that by 2.5 µg/kg of rHuEPO. These results suggested more potent erythropoietic stimulation by rHuEPO-Fc than rHuEPO.

Figure 5A:
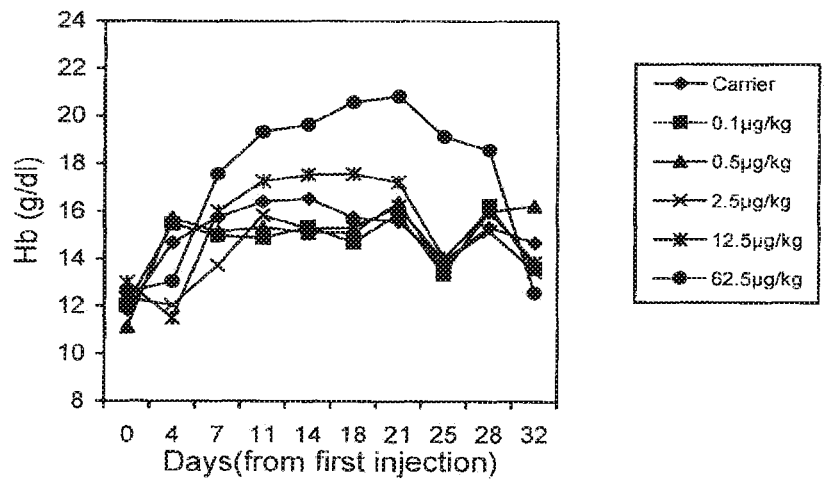
FIGS. 5A and 5B are graphs showing the dose-dependent increase of hemoglobin (Hb) levels in normal mice treated with once per week s.c. of rHuEPO-Fc or rHuEPO. Each point represents the mean Hb level of the group (6 mice). Day 0 levels represent the Hb levels before treatment.
Figure 5B:
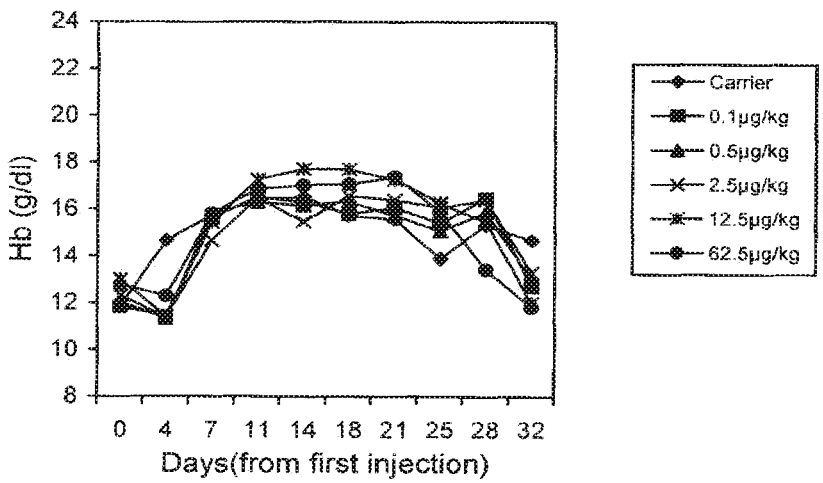

The erythropoietic potency of rHuEPO-Fc was further explored by reducing the injection times to once per week subcutaneously. As shown in FIG. 5, the rHuEPO-Fc-treated groups showed dose-dependent elevation of Hb levels at the doses of 12.5, or 62.5 µg/kg. Both doses of 12.5 and 62.5 µg/kg of rHuEPO also induced the elevation of Hb levels to the similar extent, which was much lower than that by 62.5 µg/kg of rHuEPO-Fc. This strongly indicates that rHuEPO-Fc has enhanced erythropoietic activity in vivo. It is presumably due to either the prolonged half-life of the rHuEPO-Fc in vivo or improved EPO receptor binding/activation by the dimer EPO molecules in the rHuEPO-Fc protein, or by the combined effects of both.

Figure 6A:
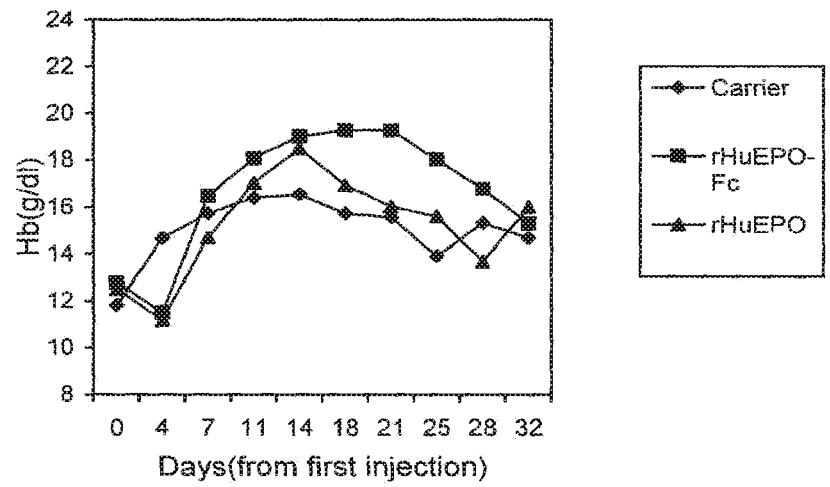
FIGS. 6A and 6B are graphs showing the increase of hemoglobin (Hb) levels in normal mice treated with intravenously injection (i.v.) of 12.5 µg/kg of rHuEPO-Fc or rHuEPO. Each point represents the mean Hb level of the group (6 mice). Day 0 levels represent the Hb levels before treatment.
Figure 6B:
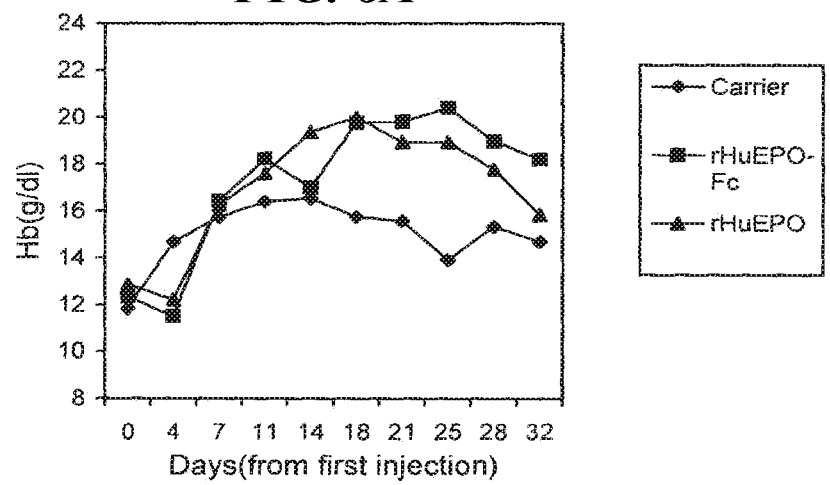

When the same doses (12.5 µg/kg) of rHuEPO-Fc or rHuEPO were administrated intravenously either three times per week or once per week, elevation of the Hb levels was observed for all the treated groups (FIG. 6). However, i.v. administration once per week of rHuEPO-Fc induced greater, more persistent elevation of the Hb levels, which continued longer after the treatment was over. This data provides further support for the enhanced erythropoietic properties of the rHuEPO-Fc protein in comparison with rHuEPO having the structure of naturally occurring EPO protein.

6. Enhanced Erythropoietic Activities of rHuEPO-Fc in 5/6 Nephrectomized Rats

Experiments in normal mice proved the enhanced erythropoietic activities of rHuEPO-Fc in vivo. To further observe the efficacy of rHuEPO-Fc in stimulating erythropoiesis, pharmacodynamic studies were conducted in rats with experimental renal anemia that was made by 5/6 nephrectomy. The efficacy of rHuEPO-Fc was compared with those of rHuEPO and darbepoetin-alpha (60 µg/ml, lot. No. N079, manufactured by Kirin Brewery Co., Japan).

Wistar rats (male and female in equal number, weighing 160-180 g, purchased from Vitalriver Experiment Animal Inc., Beijing, China. Licence No. SCXK11-00-0008) were used in this invention to create the anemia model due to the renal functional failure by a two-step nephrectomy [27]. 5/6 nephrectomy was done to rats with general anesthesia by two separate operations under sterile condition. After 2/3 of the left kidney was resected, the rats were allowed to recover for twenty days. The right kidney was then resected carefully. Antibiotics were administrated to prevent infection after each operation. In total 5/6 of the kidney tissue was finally resected. The nephrectomized rats gradually developed renal function dissufficiency and anemia. The rats entered stable status of anemia 50 days after nephrectomy, and were then randomly grouped (9/group) to start the administration of the EPOs. Each group of rats was treated with one combination of one dose (2.5, 12.5, 62.5 µg/kg), one injection route (i.v. through the tail vein or s. c.) and one injection schedule (once per week or once every 2 weeks). The control group and model group of rats were injected with the equal volume of carrier solution. The treatment lasted for 4 weeks and the total observation times were 6 weeks.

Figure 7:
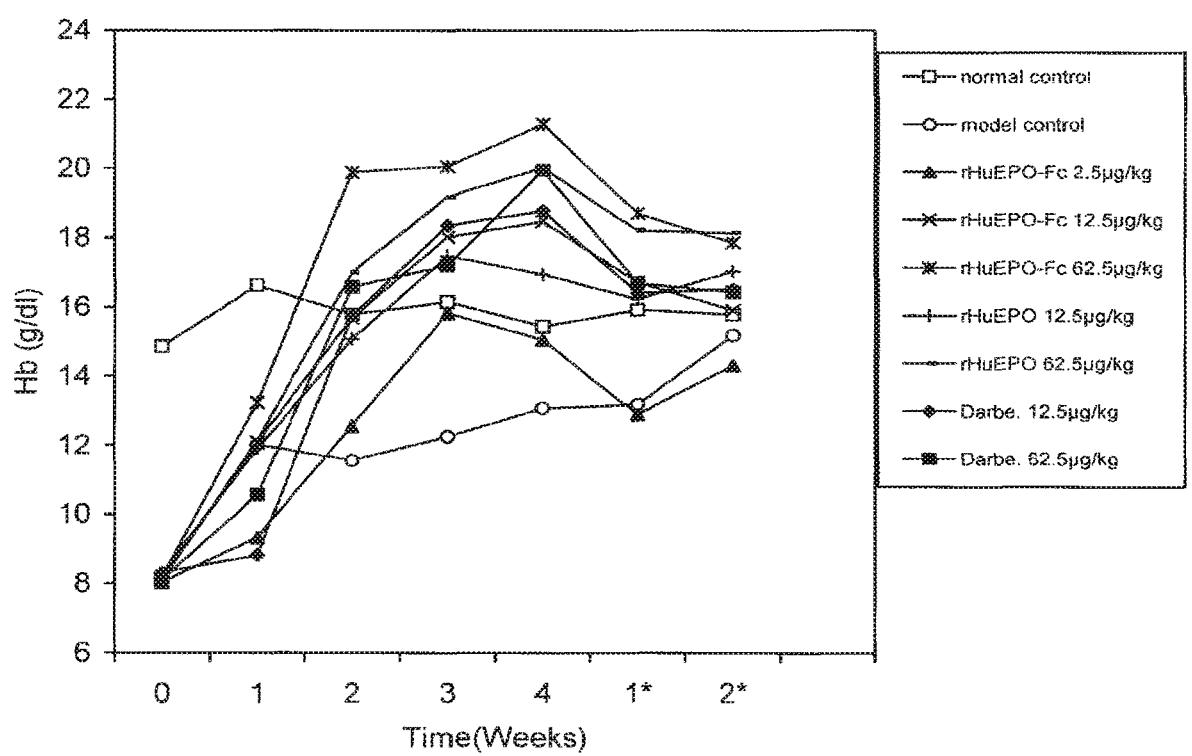
FIG. 7 is a graph showing the dose-dependent increase of hemoglobin (Hb) levels in ⅚ nephrectomized rats treated with once per week s.c. of rHuEPO-Fc, rHuEPO or darbepoetin-alfa (abbreviated Darbe.). Each point represents the mean Hb level of the group. Normal controls were normal rats with injection of carrier solution. Model controls were the ⅚ nephrectomized rats with injection of carrier solution. Week 0 levels represent the Hb levels before treatment. *: week(s) post treatment.

All doses (2.5, 12.5, 62.5 µg/kg) of rHuEPO-Fc, administered subcutaneously once per week, induced dose-dependent elevation of the Hb levels comparing to the model control group that did not receive EPO treatment. Both 12.5 and 62.5 µg/kg of rHuEPO or darbepoetin, administered subcutaneously once per week also induced elevation of Hb levels. The increased levels of Hb in both groups treated with 12.5 or 62.5 µg/kg of rHuEPO-Fc were significantly higher than those in groups treated with 12.5 or 62.5 µg/kg of rHuEPO respectively. The Hb levels in 62.5 µg/kg of rHuEPO-Fc-treated groups were also slightly higher than that in 62.5 µg/kg of darbepoetin-treated group. After stopping treatment, the decrease of Hb levels in 62.5 µg/kg of rHuEPO-Fc-treated group was much slower and the Hb levels remained higher than those of both normal control and model control groups until the end of observation (two weeks after treatment), indicating a stronger and/or a prolonged erythopoietic stimulation (summarized in FIG. 7).

Figure 8:
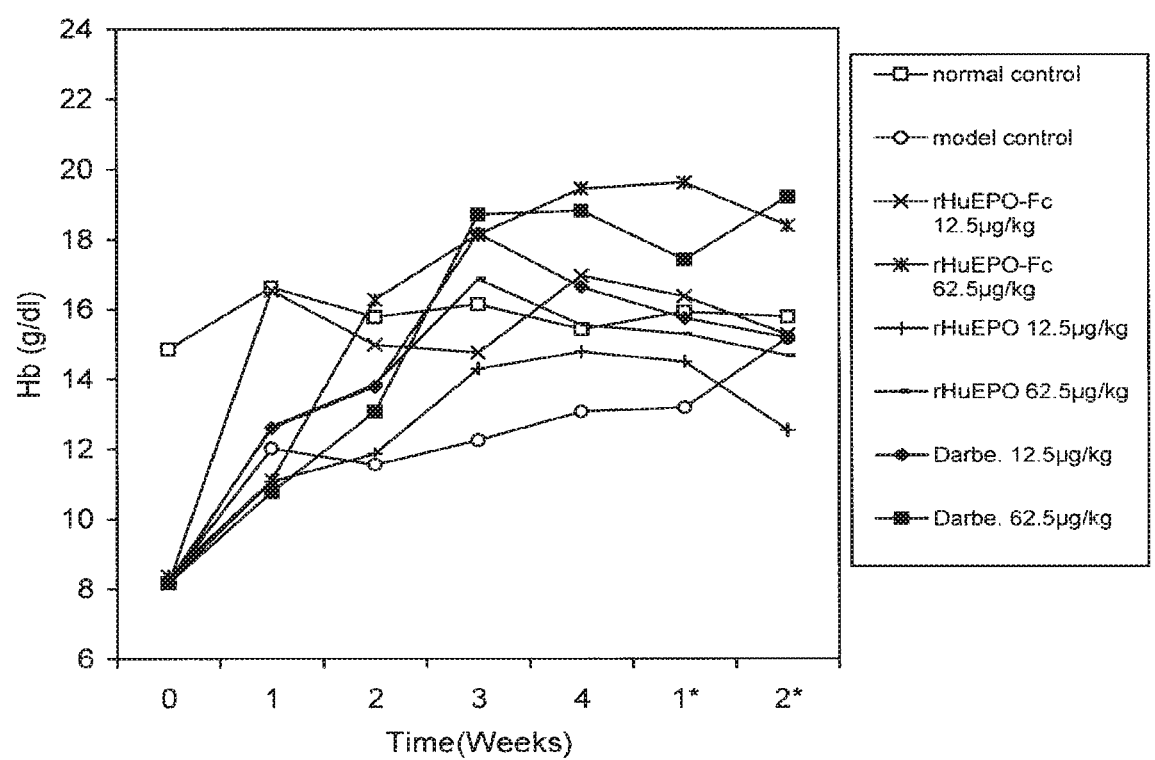
FIG. 8 is a graph showing the dose-dependent increase of hemoglobin (Hb) levels in ⅚ nephrectomized rats treated once every two weeks s.c. with rHuEPO-Fc, rHuEPO or darbepoetin-alfa (abbreviated Darbe.). Each point represents the mean Hb level of the group. Normal controls were normal rats with injection of carrier solution. Model controls were the ⅚ nephrectomized rats with injection of carrier solution. Week 0 levels represent the Hb levels before treatment. *: week(s) post treatment.

For the treatment of subcutaneous injection once every two weeks, only 12.5 or 62.5 µg/kg of the three EPOs were administered (FIG. 8). 12.5 µg/kg of rHuEPO barely increased Hb levels compared to the model control group, and the weak erythropoietic response in the 62.5 µg/kg of rHuEPO treated group failed to bring the Hb levels to normal in comparison with the normal control group. Treatments of either rHuEPO-Fc or darbepoetin at the doses of 12.5 or 62.5 µg/kg induced significant elevation of Hb levels that was higher than that of the normal control group, indicating the effective correction of anemia status by both rHuEPO-Fc and darbepoetin. No significant differences were observed between same doses of rHuEPO-Fc and darbepoetin in terms of efficacy. The high dose of 62.5 µg/kg resulted in the persistent increase of erythropoiesis until the termination of the observation (two weeks post treatment). This further suggested that rHuEPO-Fc and darbepoetin exhibit the property of long-lasting stimulation of erythropoiesis in vivo, which in turn could be transferred to the reduction of administration frequencies to patients clinically.

While darbepoetin has been approved for clinical application with less-frequent injections to increase the patient compliance and reduce the work burden of health care providers, these experimental data strongly indicate that rHuEPO-Fc disclosed in the current invention has at least the similar potential benefits. As discussed above, darbepoetin, as a mutant analog of the human EPO molecule containing additional sugar compounds (increased glycosylation), may have an increased risk of inducing immunogenesis in vivo due to the altered three dimensional structures. Only long-term observation of patients undergoing treatment with darbepoetin will give a decisive answer to the immunogenic risks of darbepoetin. In contrast, rHuEPO-Fc, without the modification of the EPO molecule portion, has a carbohydrate content identical or closely similar to that of native human EPO. The amounts of sialic acids in the inventors' pure rHuEPO-Fc protein were around 10.0 mmol/mmol EPO, consistent with the reported parameters of rHuEPO. The Fc part of rHuEPO-Fc, with no external amino acid(s)/linking peptide, represents the general structure of human IgG1, and theoretically would not lead to an immunogenic response. If approved clinically, rHuEPO-Fc may provide a better choice for patients than currently available rHuEPO and EPO analogs, especially those who need long-term administration.

Figure 9:
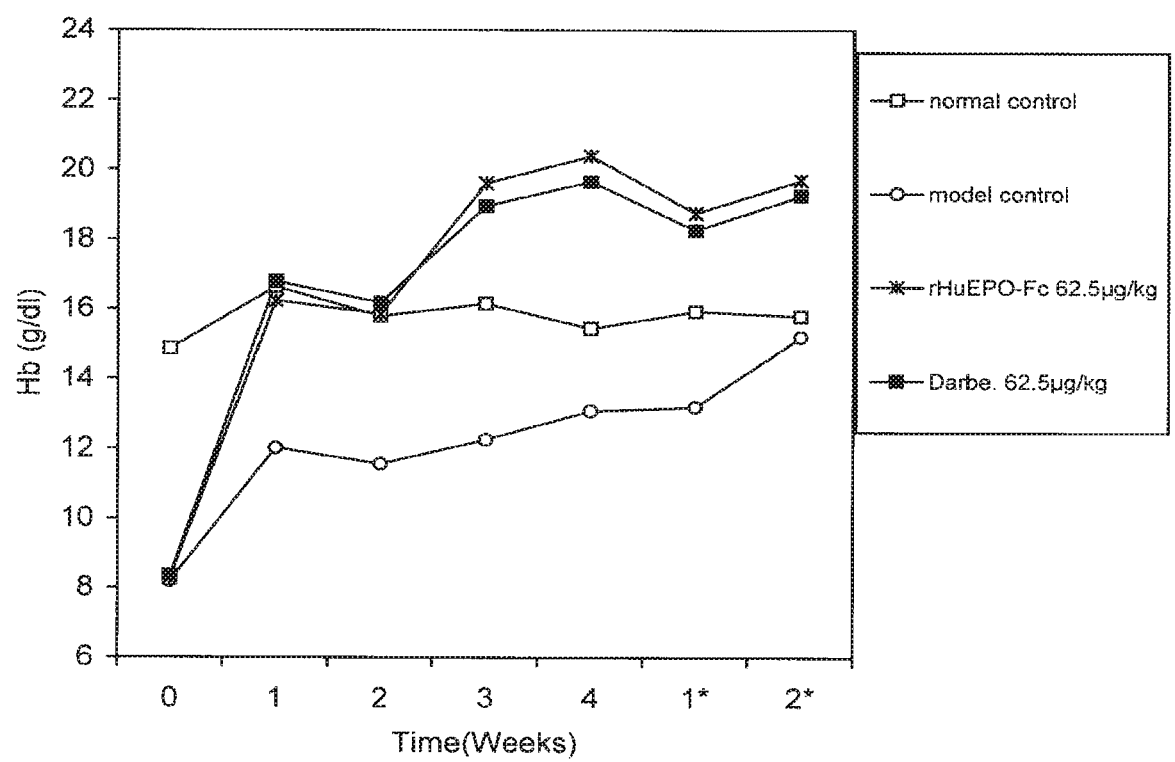
FIG. 9 is a graph showing the dose-dependent increase of hemoglobin (Hb) levels in ⅚ nephrectomized rats treated once every two weeks i.v. with 62.5 µg/kg of rHuEPO-Fc, or darbepoetin-alfa (abbreviated Darbe.). Each point represents the mean Hb level of the group. Normal controls were normal rats with injection of carrier solution. Model controls were the ⅚ nephrectomized rats with injection of carrier solution. Week 0 levels represent the Hb levels before treatment. *: week(s) post treatment.

Once injected intravenously once every two weeks, both rHuEPO-Fc and darbepoetin (62.5 m/kg) were able to induce identical increases of Hb levels in the rats with renal anemia far above the normal Hb levels in the normal control rats (FIG. 9). This further demonstrates the persistent stimulation of erythropoiesis by rHuEPO-Fc, as darbepoetin's efficacy has been clinically proven.

Figure 10A:
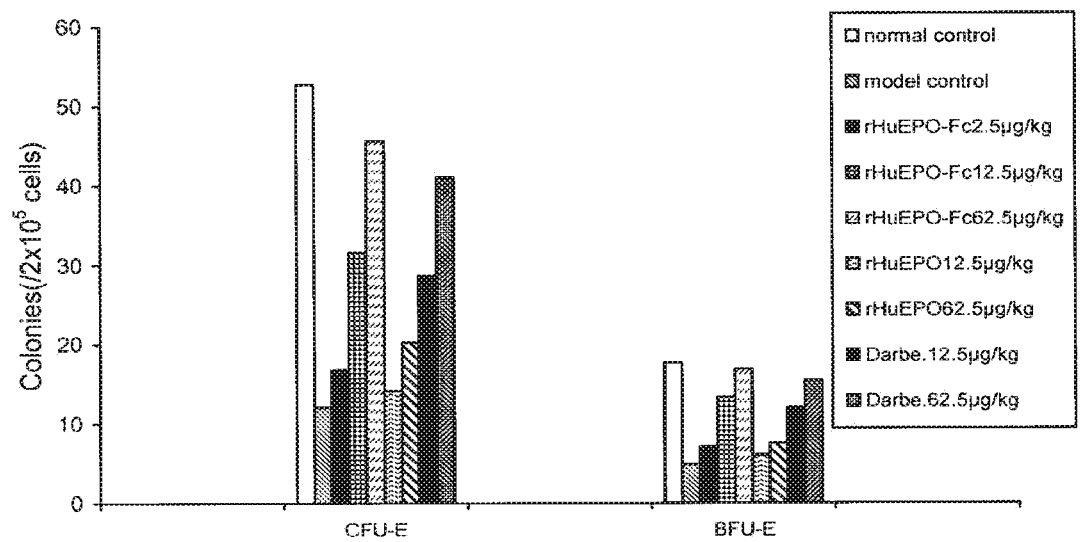
FIGS. 10A-10C show the potency comparisons of rHuEPO-Fc, rHuEPO and darbepoetin-alfa for stimulating the colony formation of CFU-E and BFU-E in ⅚ nephrectomized rats treated with different doses and schedules. rHuEPO-Fc and darbepoietin-alpha (abbreviated Darbe.) treatment showed similar dose-dependent potencies for stimulating the CFU-E and BFU-E colony formation, while rHuEPO was less potent.
Figure 10B:
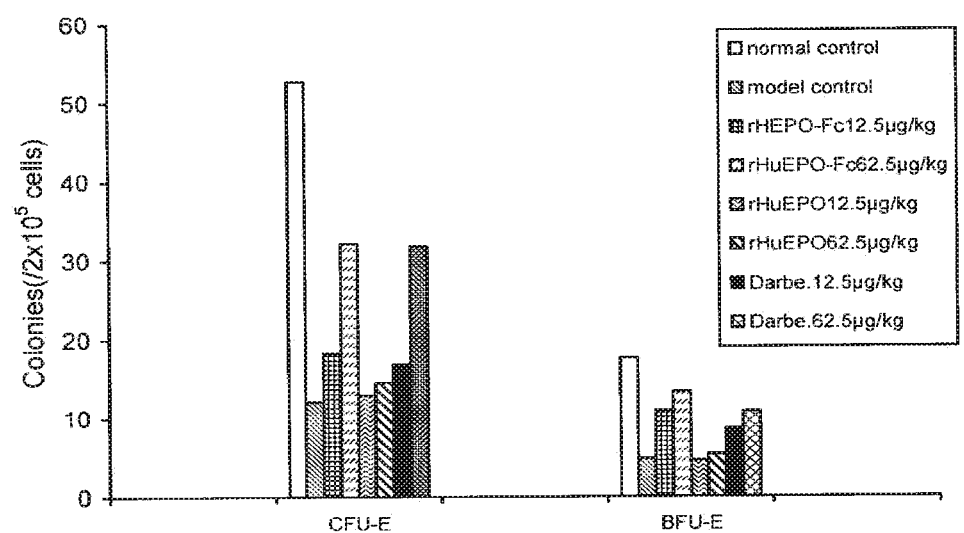
Figure 10C:
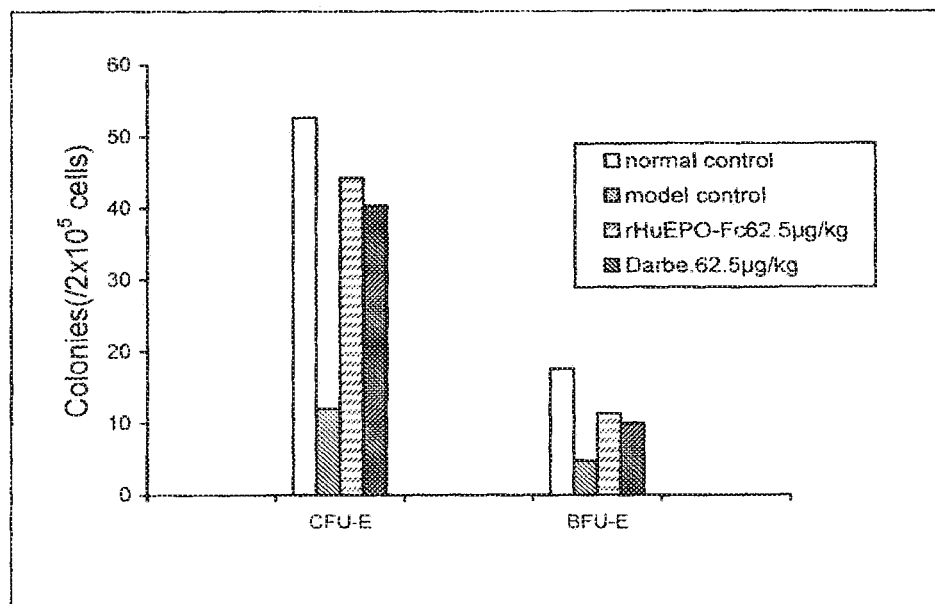

Data derived from cell culturing experiments of bone marrow cells collected from the 5/6 nephrectomized rats after treatments (once per week or per two weeks, s.c. or i.v.) showed that rHuEPO-Fc, rHuEPO and darbepoetin all stimulated the formation of CFU-E and BFU-E. The potencies of rHuEPO-Fc and darbepoetin were similar and stronger than that of rHuEPO (FIG. 10).

Blood urinonitrogen (BUN) and Crea levels were similar in the treated groups and model control group. The levels of serum Fe in all the treated groups were higher that that of the model control group. Pathological examinations observed the increase distribution of red blood cell (RBC)-related cells in bone marrow and spleen of all EPO-treated rats.

7. Pharmacokinetic Studies of rHuEPO-Fc in Rhesus Monkeys

As discussed above, the inventors have designed rHuEPO-Fc in such way that the EPO portion of the fusion protein retains the functional properties of natural EPO, such as stimulating erythropoiesis, and the Fc fragment of human IgG1 allows the stable existence of the fusion protein in circulation, thus extending its half-life in vivo. The above animal studies have demonstrated the erythropoietic activities of rHuEPO-Fc are enhanced in comparison with rHuEPO. The inventors have also conducted pharmacokinetic studies to determine the in vivo half-life of rHuEPO-Fc in comparison to that of rHuEPO. Primates were used to generate data as they are biologically very similar to human beings.

Figure 11:
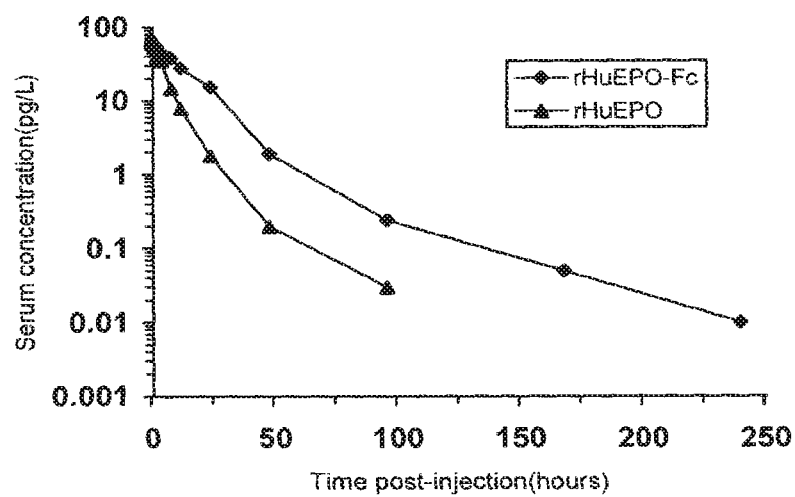
FIG. 11 is a graph showing the serum levels of rHuEPO-Fc and rHuEPO after the intraveous injection of 5 µg/kg of rHuEPO-Fc or rHuEPO to Rhesus monkeys (mean levels of 5 monkeys).

Study design was based on literature reports and the experiments were conducted according to the general guidelines of pharmacokinetics. Two groups of Rhesus monkeys with 5 monkeys in each group (3-5 kg, purchased from the Experiment Animal Center, AMMS, China) were injected intravenously with 5 µg/kg of rHuEPO-Fc or rHuEPO, respectively. Blood samples were taken before and at 0.017, 0.167, 0.5, 1, 2, 4, 8, 12, 24, 48, 96, 168, 240 h after injection. Sera were collected by centrifugation and the serum rHuEPO-Fc or rHuEPO levels were determined by using human erythropoietin enzyme-linked immunosorbent assay (ELISA) kits (purchased from R&D Systems, Minneapolis, Minn.). The average half-life (t1/2) of rHuEPO-Fc and rHuEPO injected intravenously was 35.24+/−5.15 h and 8.72+/−1.69 h respectively (summarized in FIG. 11).

To observe the bioavailability of rHuEPO-Fc, 5 ug/kg of rHuEPO-Fc was injected subcutaneously to 5 Rhesus monkeys. Blood samples were taken before and 1, 2, 5, 8, 10, 12, 15, 24, 48, 72, 96, 168, 240 h after the injection, and the serum levels of rHuEPO-Fc were determined by the R&D kits. The bioavailability index was calculated as 35.71+/−5.37% with the subcutaneous injection. This is identical to the reported bioavailability figures of darbepoetin-alpha (ARANESP™) in patients with chronic renal failure [9, 15].

This data demonstrates that rHuEPO-Fc has a significantly prolonged half-life in primates, and the in vivo half-life of rHuEPO-Fc is at least four fold longer than that of rHuEPO manufactured by Kirin Beer Brewing Co. of Japan. The prolonged half-life in vivo likely contributes to the enhanced erythropoietic activity of rHuEPO-Fc.

8. Immunogenicity of rHuEPO-Fc in *Macaca fascicularis*

As indicated above, attention was given in the design of rHuEPO-Fc fusion protein to intentionally avoid or minimize the changes of the immunogenic properties of the rHuEPO-Fc fusion protein. The inventors avoided including/adding any external amino acid(s) or linking peptide sequences in the fusion protein. The invented HuEPO-Fc fusion protein of the embodiment of FIG. 1B only contains the polypeptide sequences of the natural EPO protein and the Fc fragment (hinge region, CH2, CH3) of human IgG1, and would theoretically not induce an immunogenic response and the production of antibodies against rHuEPO-Fc protein. As will be appreciated by a person skilled in the art, other embodiments having alternative structures are also encompassed by the present invention.

The following primate studies were conducted to observe the immunogenicity of rHuEPO-Fc protein. Ten crab-eating macaque (*Macaca fascicularis*)(male/female=5/5, ~5 years old, average weight of male 4.0±0.3 kg, female is 2.9±0.4 kg, purchased from Laboratory Animal Center, AMMS, China) were injected subcutaneously with 5 µg/kg of purified rHuEPO-Fc 3 times per week for 4 weeks, and two were injected with equal volume of carrier solution as the control animals. Sera were collected once a week for 5 weeks (1 week post-treatment) and tested for the specific antibodies against rHuEPO-Fc by ELISA using the purified rHuEPO-Fc (5 µm/ml) as the coating antigen. In addition, RBC count and Hb levels in the peripheral blood were also determined within the experimental period. The resultant data shows that, while the stimulated erythropoiesis enhancement in the rHuEPO-Fc-treated macaques was observed (the mean RBC numbers increased from 4.74×10$^9$/ml to 6.67×10$^9$/ml and the mean Hb levels from 12.2 g/dl to 13.7 g/dl), rHuEPO-Fc failed to induce detectable specific antibodies against the fusion protein. These results indicate that rHuEPO-Fc fusion protein does not cause immunogenicity in primates.

9. Acute Toxicity Studies of rHuEPO-Fc in Normal Mice

To assess the safety of rHuEPO-Fc fusion protein, acute toxic studies were conducted in animals.

Two groups of BALB/c mice (n=20, equal numbers of male and female, 5-6 weeks old, the average weight of female is 15.8±0.4 g, male is 15.9±0.6 g, purchased from Chinese Academy of Medicine, China) were injected intravenously once with excessive amount of purified rHuEPO-Fc (male=13.3 mg/kg, female=13.2 mg/kg) or equal volume of the carrier solution via their tail veins respectively. In addition to observing the instant reaction following injection, general behavior and status, activities, eating and defecation patterns and changes were monitored and recorded daily for 14 days. All mice were also weighed at day 7 and day 14. At day 15 post-injection, the anatomic examination of the main organs of the mice were conducted. Pathologic examination would be conducted if any unusual changes or suspicious changes of the organs were observed.

All mice in the 2 groups had no obvious instant reaction following injection. Within the period of 14 days, no obvious changes of behavior, activities, eating and defecation patterns were observed. Moreover, the weight of the mice in both groups increased steadily during the testing period, and no apparent differences were found between the 2 groups on day 7 or day 14 post injection. No abnormal or pathologic changes were detected in the tissues of brain, lung, heart, liver and kidney. These results indicate that administration of excessive amount of rHuEPO-Fc, far more than required for exhibiting the normal erythropoiesis function, is safe and had no apparent toxic effects.

10. Comparison of Wild Type and Mutated EPO Fusion Proteins

Investigations were also conducted to compare wild type and mutated versions of EPO proteins. As described above, in one embodiment the invention includes a single amino acid mutation at amino acid residue 172 (C172G). For comparison purposes, a wild type fusion protein was also prepared having a cysteine amino acid at residue 172 (FIG. 12). The wild type fusion protein was prepared in the same manner as Examples 1-3 above. With respect to the construction of the recombinant plasmid, the following oligo primers (QIAGEN Inc., US) were used (the altered amino acids in EFL5w and EFL3w in comparison to the primers of Example 1 are bolded):

```
EF5:
5'-ccggaattcgccaccatgggggtgcacgaatgtcctgcct-3';

EF3:
5'-ttttccttttgcggccgcttatttacccggagacagggagag-3';

EFL5w:
5'-aggcctgcaggacaggggacagagttgagcccaaatcttgtgaca-3';

EFL3w:
5'-tgtcacaagatttgggctcaactctgtccctgtcctgcaggcct-3'.
```

The sequences of primers EFL5w and EFL3w are listed in SEQ ID NO:9 and SEQ ID NO:10, respectively. The sequences of primers EF5 and EF3 are listed in SEQ ID NO:5 and SEQ ID NO:6, respectively.

In vivo experiments in mice were conducted to compare the erythropoietic activity of the wild type fusion protein (herein referred to as rHuEPO-FcC) with the mutated fusion protein (i.e. the rHuEPO-Fc protein of the present invention described above) and with recombinant human EPO (rHuEPO). For comparison purpose, all the doses of the three proteins used in this example, namely rHuEPO-Fc, rHuEPO-FcC and rHuEPO, were the amounts of the EPO molecule portion alone on a molar basis. In respect to the rHuEPO-Fc and rHuEPO-FcC proteins, the EPO portion contributes to 41.4% of the total molecular weight as calculated by the ratio of the weight of amino acids of EPO to the weight of the total amino acids of the whole rHuEPO-Fc and rHuEPO-FcC molecules (i.e. 166 aa among 399 aa).

rHuEPO-Fc (stock concentration: 300 µg/ml), rHuEPO-FcC (stock concentration: 90 µg/ml) and rHuEPO with the natural human EPO structure (6000 IU/0.5 ml, manufactured by Kirin Brewery Co., Japan) were diluted in carrier solution (2.5 mg/ml of human serum albumin, 5.8 mg/ml of sodium citrate, 0.06 mg/ml of citric acid and 5.8 mg/ml of sodium chloride, pH 5.5-5.6). The dose of rHuEPO in amount was calculated according to its activity/amount ratio. BALB/c mice (9- to 10-week old, weighing 18-22 g, equal numbers of male and female, purchased from Experiment Animal Center, AMMS, China) were grouped randomly with 8 in each group. Each group of mice was treated with one combination of one dose (2.5, 12.5, 62.5 µg/kg), one injection route (s. c.) and one injection schedule (three times per week or once per week). The control group of mice was injected with the equal volume of carrier solution. The treatment lasted for 26 days. Peripheral blood samples (tail vein) for measurement were taken before treatment, on the $2^{nd}$, $6^{th}$, $9^{th}$, $13^{th}$, $16^{th}$, $19^{th}$, $22^{nd}$ and $26^{th}$ days of treatment. Hb was measured as the index by absorptiometry. Mean±SD was calculated from the data of each group and t test was conducted among different groups.

Figure 13:
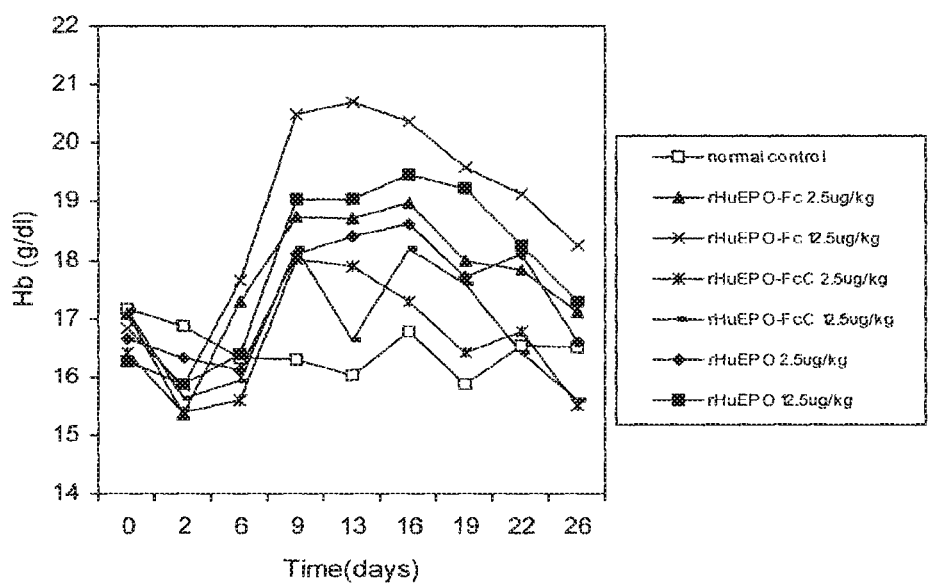
FIG. 13 is a graph showing dose-dependent increase of hemoglobin (Hb) levels in normal mice treated with three times per week subcutaneous injection (s. c.) of rHuEPO-Fc (the mutant fusion protein of the present invention), rHuEPO-FcC (the wild type fusion protein) and rHuEPO. Each point represents the mean Hb level of the group (8). Normal control were normal mice with injection of carrier solution. Day 0 levels represent the Hb levels before treatment.

As shown in FIG. 13, administration of all three EPO proteins at intervals of three times per week stimulated erythropoiesis. At either the dose of 2.5 µg/kg or 12.5 µg/kg, rHuEPO-Fc induced higher elevation of Hb levels than rHuEPO. The highest elevation of Hb levels was achieved by the 12.5 µg/kg dose of rHuEPO-Fc. Both the 2.5 µg/kg and 12.5 µg/kg doses of rHuEPO-FcC induced much weaker erythropoiesis than equivalent doses of rHuEPO and rHuEPO-Fc as indicated by the significant lower elevation of Hb levels in the rHuEPO-FcC-treated groups. In fact, 12.5 µg/kg of rHuEPO-FcC induced lower elevation of Hb levels than 2.5 µg/kg of rHuEPO. These results suggest that rHuEPO-FcC has impaired erythropoietic activity in vivo in comparison to rHuEPO having the natural EPO molecular sequence. By contrast, the rHuEPO-Fc fusion protein of the present invention exhibited more potent erythropietic functions. The administration of the three EPO proteins at intervals of three times per week largely excluded the impact of differences in the half-life of the proteins.

Figure 14:
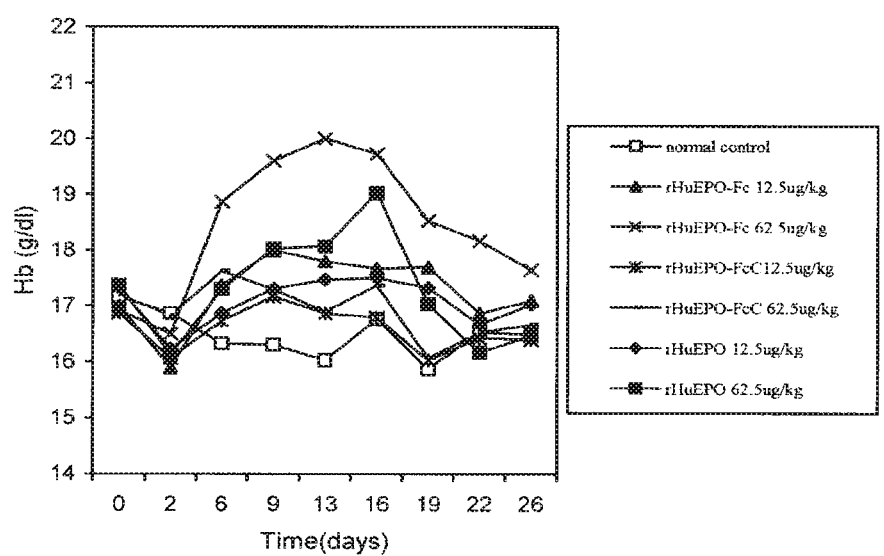
FIG. 14 is a graph showing dose-dependent increase of hemoglobin (Hb) levels in normal mice treated with once per week subcutaneous injection (s. c.) of rHuEPO-Fc, rHuEPO-FcC and rHuEPO. Each point represents the mean Hb level of the group (8). Normal control were normal mice with injection of carrier solution. Day 0 levels represent the Hb levels before treatment.

The erythropoietic potency of rHuEPO-Fc and rHuEPO-FcC was further evaluated by reducing the injection times to once per week subcutaneously. As shown in FIG. 14, the rHuEPO-Fc-treated groups showed higher elevation of Hb levels than rHuEPO-treated ones at the doses of 12.5 µg/kg or 62.5 µg/kg. In contrast, rHuEPO-FcC induced much weaker elevation of Hb levels than that induced by rHuEPO. For example, 12.5 µgkg of rHuEPO induced higher elevation of Hb levels than that induced by 62.5 µg/kg of rHuEPO-FcC at most time points. This further indicates that by reducing the administration times to include the effects of half-life, rHuEPO-FcC exhibits much weaker erythropoietic functions in vivo in comparison to rHuEPO having the natural EPO molecular sequence and in comparison to the rHuEPO-Fc fusion protein of the present invention.

In summary, these results demonstrate that rHuEPO-FcC, formed by the fusion of natural molecular sequences of both human EPO and human Fc fragment (hinge, CH2 and CH3), exhibits much weaker erythropoietic functions in vivo in comparison to the rHuEPO having the natural EPO molecular sequence. In particular, the erythropoietic activities of the rHuEPO-FcC fusion protein are less than ⅕ of those of natural EPO molecule. This indicates that the fusion between EPO molecule and the natural sequence of human Fc fragment impairs the functional properties of the EPO molecule. By the single amino acid replacement at the first cysteine residue in the hinge region of the Fc fragment, the rHuEPO-Fc fusion protein of the present invention comprising the natural EPO molecule sequence and the mutant Fc fragment shows more potent erythropoietic functions in vivo compared to the natural EPO molecule. This data suggests that the first cysteine residue in the hinge region of the wild type Fc fragment somehow interferes with the EPO molecule, likely by causing structural changes to the EPO molecule, and this in turn impairs the functional properties of the EPO molecule in stimulating erythropoiesis.

As will be apparent to those skilled in the art in the light of the foregoing disclosure, many alterations and modifications are possible in the practice of this invention without departing from the spirit or scope thereof.

REFERENCES

1. Cohen J, et al. Erythropoietin and its receptor: signaling and clinical manifestations. IMAJ 4, pp 1072-1076(2002)
2. Blackwell K, et al. rHuEPO and improved treatment outcomes: potential modes of action. The Oncologist 9(suppl 5), pp 41-47 (2004).
3. Lappin T R, et al. EPO's alter ego: erythropoietion has multiple actions. Stem Cells 20, pp 485-492 (2002).
4. Maiese K, et al. New avenues of exploration for erythropoietin. JAMA 293(1), pp 90-95(2005).
5. Fisher J W. Erythropoietin: physiologic and pharmacologic aspects. Proc. Soc. Exp. Biol. Med. 216, pp 358-369 (1997).
6. Jelkmann W. Molecular biology of erythropoietin. Internal Med. 43(8), pp 649-659 (2004).
7. Ng T, et al. Recombinant erythropoietin in clinical practice. Postgrad. Med. J. 79, pp 367-376 (2005).
8. Weiss G, et al. Anemia of chronic disease. N. Engl. J. Med. 352(10), pp 1011-1023 (2005).
9. Macdougall I C. An overview of the efficacy and safety of novel erythropoiesis stimulating protein (NESP). Nephrol. Dial. Transplant. 16(suppl 3), pp 14-21 (2001).
10. Joy M S. Darbepoetin-alfa: a novel erythropoiesis-stimulating protein. Ann. Pharmacother. 36, pp 1183-1192 (2002).
11. Ellitt S, et al. Enhancement of therapeutic protein in vivo activities through glycoengineering. Nature Biotechnology 21, pp 414-421 (2003).
12. Elliott S, et al. Control of rHuEPO biological activity: the role of carbohydrate. Experimental Hematology 32, pp 1146-1155 (2004).
13. Egrie J C, et al. Darbepoetin-alfa has a longer circulating half-life and greater in vivo potency than recombinant human erythropoietin. Exp. Hematol. 31, pp 290-299 (2003).
14. Egrie J C, et al. Development and characterization of novel erythropoiesis stimulating protein (NESP). British J. Caner. 84(suppl 1), pp 3-10 (2001).

15. Macdougall I C, et al. Pharmacokinetics of novel erythropoiesis stimulating protein compared with epoetin alfa in dialysis patients. J. Am. Soc. Nephrol. 10, pp 2392-2395 (1999).
16. Jolling K, et al. Population pharmacokinetic analysis of peglated human erythropoietin in rats. J. Pharm. Sci. 93(12), pp 3027-3038 (2004)
17. Dalle B, et al. Dimeric erythropoietin fusion protein with enhanced erythropoietic activity in vtro and in vivo. Blood 97(12), pp 3776-3782 (2001).
18. Kochendoerfer G G, et al. Design and chemical synthesis of a homogeneous polymer-modified erythropoiesis protein. Science 299 pp 884-887 (2003).
19. Sytkowski A J, et al. Human erythropoietin dimmers with markedly enhanced in vivo activity. Proc. Natl. Acad. Sci. USA 95, pp 1184-1188 (1998).
20. Sytkowski A J, et al. An erythropoietin fusion protein comprised of identical repeating domains exhibits enhanced biological proterties. J. Biol. Chem. 274(35), pp 24773-24778 (1999).
21. Jones T D, et al. The development of a modified human IFN-α2b linked to the Fc portion of human IgG1 as a novel potential therapeutic for the treatment of hepatitis C virus infection. J. Interferon. Cytokine. Res. 24, pp 560-572 (2004).
22. Lo K M, et al. High level expression and secretion of Fc-X fusion proteins in mammalian cells. Protein engineering 11(6), pp 495-500 (1998).
23. Mohler K M, et al. Soluble tumor necrosis factor (TNF) receptors are effective therapeutic agents in lethal endotoxemia and function simultaneously as both TNF carriers and TNF antabonists. J. Immunol. 151(3), pp 1548-1561 (1993).
24. Way J C, et al. Improvement of Fc-erythropoietin structure and pharmacokinetics by modification at a disulfide bond. Protein Engineering, Design & Selection 18(3), pp 111-118 (2005).
25. Goldenberg M M. Etanercept, a novel drug for the treatment of patients with severe, active rheumatoid arthritis. Clin. Ther. 21(1), pp 75-87 (1999)
26. Wong V K, et al. The use of alefacept in the treatment of psoriasis. Skin Therapy Lett. 8(6), pp 1-2 (2003)
27. Chanutin A, et al. Experimental renal insufficiency produced by partial nephrectomy. Arch. Intern. Med. 49, pp 767-787 (1932).

What is claimed is:

1. A fusion protein comprising:
   (a) an erythropoietin molecule having a cysteine residue near the C-terminal thereof; and
   (b) a Fc fragment comprising a mutated IgG1 hinge region, wherein the N-terminal of said Fc fragment is directly linked to said C-terminal of said erythropoietin molecule such that no external peptide linkers are interposed therebetween, provided that said mutated IgG1 hinge region has a mutation whereby a cysteine residue nearest to said N-terminal of said Fc fragment is replaced with a non-cysteine residue,
   wherein said fusion protein has the amino acid sequence present in SEQ ID NO:2 or a sequence having at least 98% sequence identity thereto, and
   wherein said fusion protein has enhanced erythropoietic activity in comparison to native human erythropoietin.

2. The protein as defined in claim 1, wherein said protein has a prolonged half-life in vivo in comparison to said native human erythropoietin.

3. The protein as defined in claim 2, wherein the half-life of said protein is at least three fold higher than said native human erythropoietin.

4. The protein as defined in claim 3, wherein said half-life of said protein is at least four fold higher than native human erythropoietin.

5. A method of stimulating erythropoiesis in a mammal comprising administering to said mammal a protein as defined in claim 2.

6. The method as defined in claim 5, wherein said mammal is a primate.

7. The method as defined in claim 6, wherein said primate is a human.

8. A method as defined in claim 5, wherein the half-life of said protein in said mammal is at least three fold higher than native human EPO when administered intravenously or subcutaneously.

9. The method as defined in claim 8, wherein the half-life of said protein in said mammal is at least four fold higher than native human EPO when administered intravenously or subcutaneously.

10. A multimeric protein construct comprising a plurality of fusion proteins as defined in claim 1.

11. The multimeric protein construct of claim 10, wherein said construct is a dimer.

12. A pharmaceutical composition comprising a protein as defined in claim 1 together with a pharmaceutically acceptable carrier, adjuvant or diluent.

13. A method of stimulating erythropoiesis in a mammal comprising administering to said mammal a pharmaceutical composition as defined in claim 12.

14. The method as defined in claim 13, wherein said mammal is a primate.

15. The method as defined in claim 14, wherein said primate is a human.

16. The fusion protein as defined in claim 1, wherein said hinge region has a non-cysteine residue at amino acid 6 measured from the N-terminal of said hinge region.

17. The fusion protein as defined in claim 16, wherein said non-cysteine residue is a neutral amino acid.

18. The fusion protein as defined in claim 17, wherein said non-cysteine residue is glycine.

19. The fusion protein as defined in claim 1, wherein said Fc fragment is a human IgG1 Fc fragment comprising a mutated human IgG1 hinge and human IgG1 CH2 and CH3 domains.

20. A fusion protein comprising:
(a) an erythropoietin molecule having a cysteine residue near the C-terminal thereof; and
(b) a Fc fragment comprising a mutated IgG1 hinge region, wherein the N-terminal of said Fc fragment is directly linked to said C-terminal of said erythropoietin molecule such that no external peptide linkers are interposed therebetween, provided that said mutated IgG1 hinge region has a mutation whereby a cysteine residue nearest to said N-terminal of said Fc fragment is replaced with a non-cysteine residue,
wherein said fusion protein has the amino acid sequence present in SEQ ID NO:2 or a sequence having at least 90% sequence identity thereto,
wherein said fusion protein has enhanced erythropoietic activity in comparison to native human erythropoietin,
and wherein hinge region has the amino acid sequence present in SEQ ID NO:17 (VEPKSGDKTSTCPPCP) or a sequence having at least 90% sequence identity thereto and having a non-cysteine residue at amino acid 6 measured from the N-terminal of said hinge region.

* * * * *

SEQUENCE LISTING

```
<160> NUMBER OF SEQ ID NOS: 18

<210> SEQ ID NO 1
<211> LENGTH: 1200
<212> TYPE: DNA
<213> ORGANISM: Artificial
<220> FEATURE:
<223> OTHER INFORMATION: DNA encoding rHuEPO-Fc fusion protein

<400> SEQUENCE: 1
gccccaccac gcctcatctg tgacagccga gtcctggaga ggtacctctt ggaggccaag      60
gaggccgaga atatcacgac gggctgtgct gaacactgca gcttgaatga aatatcact     120 gtcccagaca ccaaagttaa tttctatgcc tggaagagga tggaggtcgg gcagcaggcc    180
gtagaagtct ggcagggcct ggccctgctg tcggaagctg tcctgcgggg ccaggccctg    240
ttggtcaact cttcccagcc gtgggagccc ctgcagctgc atgtggataa agccgtcagt    300
ggccttcgca gcctcaccac tctgcttcgg gctctgcgag cccagaagga agccatctcc    360
cctccagatg cggcctcagc tgctccactc cgaacaatca ctgctgacac tttccgcaaa    420
ctcttccgag tctactccaa tttcctccgg ggaaagctga agctgtacac aggggaggcc    480
tgcaggacag gggacagagt tgagcccaaa tctggtgaca aaactagtac atgcccaccg    540
tgcccagcac ctgaactcct gggggaccg tcagtcttcc tcttccccc aaaacccaag     600 gacaccctca tgatctcccg gacccctgag gtcacatgcg tggtggtgga cgtgagccac    660
gaagaccctg aggtcaagtt caactggtac gtggacggcg tggaggtgca taatgccaag    720
acaaagccgc gggaggagca gtacaacagc acgtaccgtg tggtcagcgt cctcaccgtc    780
ctgcaccagg actggctgaa tggcaaggag tacaagtgca aggtctccaa caaagccctc    840
ccagccccca tcgagaaaac catctccaaa gccaagggc agccccgaga accacaggtg    900
tacaccctgc ccccatcccg ggatgagctg accaagaacc aggtcagcct gacctgcctg    960
gtcaaaggct tctatcccag cgacatcgcc gtggagtggg agagcaatgg gcagccggag   1020
aacaactaca agaccacgcc tcccgtgctg gactccgacg gccccttctt cctctacagc   1080
aagctcaccg tggacaagag caggtggcag caggggaacg tcttctcatg ctccgtgatg   1140
```

```
catgaggctc tgcacaacca ctacacgcag aagagcctct ccctgtctcc gggtaaataa    1200
```

```
<210> SEQ ID NO 2
<211> LENGTH: 399
<212> TYPE: PRT
<213> ORGANISM: Artificial
<220> FEATURE:
<223> OTHER INFORMATION: amino acid sequence of rHuEPO-Fc fusion protein

<400> SEQUENCE: 2
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Arg Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg Val Glu Pro Lys Ser Gly Asp Lys Thr Ser
                165                 170                 175

Thr Cys Pro Pro Cys Pro Ala Pro Glu Leu Leu Gly Gly Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser His Glu Asp Pro Glu
    210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Asp Glu Leu Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Pro Phe Phe Leu Tyr Ser Lys Leu Thr Val Asp Lys Ser Arg

```
                355                 360                 365
Trp Gln Gln Gly Asn Val Phe Ser Cys Ser Val Met His Glu Ala Leu
        370                 375                 380

His Asn His Tyr Thr Gln Lys Ser Leu Ser Leu Ser Pro Gly Lys
385                 390                 395
```

<210> SEQ ID NO 3
<211> LENGTH: 1281
<212> TYPE: DNA
<213> ORGANISM: Artificial
<220> FEATURE:
<223> OTHER INFORMATION: DNA encoding rHuEPO-Fc fusion protein with 27
    amino acid signal peptide

<400> SEQUENCE: 3

```
atggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata agccgtcag tggccttcgc agcctcacca ctctgcttcg ggctctgcga    420
gcccagaagg aagccatctc ccctccagat gcggcctcag ctgctccact ccgaacaatc    480
actgctgaca ctttccgcaa actcttccga gtctactcca atttcctccg ggaaagctg     540 aagctgtaca cagggggaggc ctgcaggaca ggggacagag ttgagcccaa atctggtgac    600
aaaactagta catgcccacc gtgcccagca cctgaactcc tggggggacc gtcagtcttc    660
ctcttccccc caaaacccaa ggacaccctc atgatctccc ggacccctga ggtcacatgc    720
gtggtggtgg acgtgagcca cgaagaccct gaggtcaagt tcaactggta cgtggacggc    780
gtggaggtgc ataatgccaa gacaaagccg cgggaggagc agtacaacag cacgtaccgt    840
gtggtcagcg tcctcaccgt cctgcaccag gactggctga atggcaagga gtacaagtgc    900
aaggtctcca acaaagccct cccagccccc atcgagaaaa ccatctccaa agccaaaggg    960
cagccccgag aaccacaggt gtacaccctg cccccatccc gggatgagct gaccaagaac   1020
caggtcagcc tgacctgcct ggtcaaaggc ttctatccca gcgacatcgc cgtggagtgg   1080
gagagcaatg ggcagccgga gaacaactac aagaccacgc ctcccgtgct ggactccgac   1140
ggccccttct cctctacag caagctcacc gtggacaaga gcaggtggca gcaggggaac   1200
gtcttctcat gctccgtgat gcatgaggct ctgcacaacc actacacgca gaagagcctc   1260
tccctgtctc cgggtaaata a                                             1281
```

<210> SEQ ID NO 4
<211> LENGTH: 426
<212> TYPE: PRT
<213> ORGANISM: Artificial
<220> FEATURE:
<223> OTHER INFORMATION: amino acid sequence of rHuEPO-Fc fusion protein
    with 27 amino acid signal peptide

<400> SEQUENCE: 4

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30
```

```
Ile Cys Asp Ser Arg Val Leu Glu Arg Tyr Leu Leu Glu Ala Lys Glu
         35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Arg Ala Gln Lys Glu
                130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                    165                 170                 175

Arg Gly Lys Leu Lys Leu Tyr Thr Gly Glu Ala Cys Arg Thr Gly Asp
                180                 185                 190

Arg Val Glu Pro Lys Ser Gly Asp Lys Thr Ser Thr Cys Pro Pro Cys
                195                 200                 205

Pro Ala Pro Glu Leu Leu Gly Gly Pro Ser Val Phe Leu Phe Pro Pro
210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
                260                 265                 270

Glu Gln Tyr Asn Ser Thr Tyr Arg Val Val Ser Val Leu Thr Val Leu
        275                 280                 285

His Gln Asp Trp Leu Asn Gly Lys Glu Tyr Lys Cys Lys Val Ser Asn
        290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

Leu Thr Lys Asn Gln Val Ser Leu Thr Cys Leu Val Lys Gly Phe Tyr
                340                 345                 350

Pro Ser Asp Ile Ala Val Glu Trp Glu Ser Asn Gly Gln Pro Glu Asn
                355                 360                 365

Asn Tyr Lys Thr Thr Pro Pro Val Leu Asp Ser Asp Gly Pro Phe Phe
370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415

Gln Lys Ser Leu Ser Leu Ser Pro Gly Lys
                420                 425

<210> SEQ ID NO 5
<211> LENGTH: 40
```

```
<212> TYPE: DNA
<213> ORGANISM: Artificial
<220> FEATURE:
<223> OTHER INFORMATION: oligonucleotide primer

<400> SEQUENCE: 5
ccggaattcg ccaccatggg ggtgcacgaa tgtcctgcct                                40

<210> SEQ ID NO 6
<211> LENGTH: 42
<212> TYPE: DNA
<213> ORGANISM: Artificial
<220> FEATURE:
<223> OTHER INFORMATION: oligonucleotide primer

<400> SEQUENCE: 6
ttttcctttt gcggccgctt atttacccgg agacagggag ag                            42

<210> SEQ ID NO 7
<211> LENGTH: 45
<212> TYPE: DNA
<213> ORGANISM: Artificial
<220> FEATURE:
<223> OTHER INFORMATION: oligonucleotide primer

<400> SEQUENCE: 7
aggcctgcag gacagggac agagttgagc ccaaatctgg tgaca                          45

<210> SEQ ID NO 8
<211> LENGTH: 45
<212> TYPE: DNA
<213> ORGANISM: Artificial
<220> FEATURE:
<223> OTHER INFORMATION: oligonucleotide primer

<400> SEQUENCE: 8
tgtcaccaga tttgggctca actctgtccc ctgtcctgca ggcct                         45

<210> SEQ ID NO 9
<211> LENGTH: 45
<212> TYPE: DNA
<213> ORGANISM: Artificial
<220> FEATURE:
<223> OTHER INFORMATION: oligonucleotide primer

<400> SEQUENCE: 9
aggcctgcag gacagggac agagttgagc ccaaatcttg tgaca                          45

<210> SEQ ID NO 10
<211> LENGTH: 45
<212> TYPE: DNA
<213> ORGANISM: Artificial
<220> FEATURE:
<223> OTHER INFORMATION: oligonucleotide primer

<400> SEQUENCE: 10
tgtcacaaga tttgggctca actctgtccc ctgtcctgca ggcct                         45

<210> SEQ ID NO 11
<211> LENGTH: 1281
<212> TYPE: DNA
<213> ORGANISM: Homo sapiens
<220> FEATURE:
<223> OTHER INFORMATION: DNA encoding wild type rHuEPO-FcC protein

<400> SEQUENCE: 11
```

```
atggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata agccgtcag tggccttcgc agcctcacca ctctgcttcg ggctctgcga   420
gcccagaagg aagccatctc ccctccagat gcggcctcag ctgctccact ccgaacaatc   480
actgctgaca ctttccgcaa actcttccga gtctactcca atttcctccg gggaaagctg   540
aagctgtaca gggggaggc ctgcaggaca ggggacagag ttgagcccaa atcttgtgac   600
aaaactagta catgcccacc gtgcccagca cctgaactcc tggggggacc gtcagtcttc   660
ctcttccccc caaaacccaa ggacaccctc atgatctccc ggaccctga ggtcacatgc   720 gtggtggtgg acgtgagcca cgaagaccct gaggtcaagt tcaactggta cgtggacggc   780
gtggaggtgc ataatgccaa gacaaagccg cgggaggagc agtacaacag cacgtaccgt   840
gtggtcagcg tcctcaccgt cctgcaccag gactggctga atggcaagga gtacaagtgc   900
aaggtctcca acaaagccct cccagccccc atcgagaaaa ccatctccaa agccaaaggg   960
cagccccgag aaccacaggt gtacaccctg cccccatccc gggatgagct gaccaagaac  1020
caggtcagcc tgacctgcct ggtcaaaggc ttctatccca gcgacatcgc cgtggagtgg  1080
gagagcaatg ggcagccgga gaacaactac aagaccacgc tcccgtgct ggactccgac  1140 ggccccttct cctctacag caagctcacc gtggacaaga gcaggtggca gcaggggaac  1200
gtcttctcat gctccgtgat gcatgaggct ctgcacaacc actacacgca gaagagcctc  1260
tccctgtctc cgggtaaata a                                             1281
```

<210> SEQ ID NO 12  
<211> LENGTH: 426  
<212> TYPE: PRT  
<213> ORGANISM: Homo sapiens  
<220> FEATURE:  
<223> OTHER INFORMATION: amino acid sequence of wild type rHuEPO-FcC protein

<400> SEQUENCE: 12

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125
```

```
Leu Arg Ser Leu Thr Thr Leu Leu Arg Ala Leu Arg Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Val Glu Pro Lys Ser Cys Asp Lys Thr Ser Thr Cys Pro Pro Cys
        195                 200                 205

Pro Ala Pro Glu Leu Leu Gly Gly Pro Ser Val Phe Leu Phe Pro Pro
210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285

His Gln Asp Trp Leu Asn Gly Lys Glu Tyr Lys Cys Lys Val Ser Asn
290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

Leu Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
        355                 360                 365

Asn Tyr Lys Thr Thr Pro Pro Val Leu Asp Ser Asp Gly Pro Phe Phe
370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415

Gln Lys Ser Leu Ser Leu Ser Pro Gly Lys
            420                 425

<210> SEQ ID NO 13
<211> LENGTH: 10
<212> TYPE: DNA
<213> ORGANISM: Artificial Sequence
<220> FEATURE:
<223> OTHER INFORMATION: Kozak sequence

<400> SEQUENCE: 13
gccaccatgg                                                          10

<210> SEQ ID NO 14
<211> LENGTH: 15
<212> TYPE: PRT
<213> ORGANISM: Artificial
<220> FEATURE:
<223> OTHER INFORMATION: amino acid sequence of N terminal end of
      rHuEPO-Fc fusion protein

<400> SEQUENCE: 14
```

Ala Pro Pro Arg Leu Ile Cys Asp Ser Arg Val Leu Glu Arg Tyr
1               5                   10                  15

<210> SEQ ID NO 15
<211> LENGTH: 27
<212> TYPE: PRT
<213> ORGANISM: Artificial Sequence
<220> FEATURE:
<223> OTHER INFORMATION: Signal peptide

<400> SEQUENCE: 15

Met Gly Val His Glu Cys Pro Ala Trp Leu Trp Leu Leu Ser Leu
1               5                   10                  15

Leu Ser Leu Pro Leu Gly Leu Pro Val Leu Gly
            20                  25

<210> SEQ ID NO 16
<211> LENGTH: 166
<212> TYPE: PRT
<213> ORGANISM: Homo sapiens

<400> SEQUENCE: 16

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Arg Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 17
<211> LENGTH: 16
<212> TYPE: PRT
<213> ORGANISM: Artificial Sequence
<220> FEATURE:
<223> OTHER INFORMATION: Mutated hinge region

<400> SEQUENCE: 17

Val Glu Pro Lys Ser Gly Asp Lys Thr Ser Thr Cys Pro Pro Cys Pro
1               5                   10                  15

<210> SEQ ID NO 18
<211> LENGTH: 217
<212> TYPE: PRT
<213> ORGANISM: Homo sapiens

<400> SEQUENCE: 18

```
Ala Pro Glu Leu Leu Gly Gly Pro Ser Val Phe Leu Phe Pro Pro Lys
 1               5                  10                 15

Pro Lys Asp Thr Leu Met Ile Ser Arg Thr Pro Glu Val Thr Cys Val
             20                  25                 30

Val Val Asp Val Ser His Glu Asp Pro Glu Val Lys Phe Asn Trp Tyr
             35                  40                 45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                 80

Gln Asp Trp Leu Asn Gly Lys Glu Tyr Lys Cys Lys Val Ser Asn Lys
                 85                  90                 95

Ala Leu Pro Ala Pro Ile Glu Lys Thr Ile Ser Lys Ala Lys Gly Gln
                100             105                110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Pro Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215
```